US012766447B2

(12) United States Patent
Liu et al.

(10) Patent No.: US 12,766,447 B2
(45) **Date of Patent: *Oct. 20, 2026**

(54) BIOLOGICAL FILTRATION SYSTEMS AND CONTROLLING METHODS THEREOF

(71) Applicant: ALIT BIOTECH (SHANGHAI) CO., LTD., Shanghai (CN)

(72) Inventors: Yu Liu, Shanghai (CN); Rui Chen, Shanghai (CN)

(73) Assignee: ALIT BIOTECH (SHANGHAI) CO., LTD., Shanghai (CN)

( * ) Notice: Subject to any disclaimer, the term of this patent is extended or adjusted under 35 U.S.C. 154(b) by 967 days.

This patent is subject to a terminal disclaimer.

(21) Appl. No.: 18/048,505

(22) Filed: Oct. 21, 2022

(65) Prior Publication Data

US 2023/0131609 A1 Apr. 27, 2023

(30) Foreign Application Priority Data

Oct. 21, 2021 (CN) ......................... 202111226940.9
Oct. 21, 2021 (CN) ......................... 202122544210.5
(Continued)

(51) Int. Cl.
*B01D 35/26* (2006.01)
*B01D 29/60* (2006.01)
(Continued)

(52) U.S. Cl.
CPC ........... *B01D 35/26* (2013.01); *B01D 29/605* (2013.01); *B01D 35/1475* (2013.01);
(Continued)

(58) Field of Classification Search
None
See application file for complete search history.

(56) References Cited

U.S. PATENT DOCUMENTS 11,459,535 B1 * 10/2022 Yeh ........................ C12M 47/02
2004/0050789 A1 3/2004 Ash
(Continued)

FOREIGN PATENT DOCUMENTS

CN 107782657 A 3/2018
CN 211434457 U 9/2020
(Continued)

OTHER PUBLICATIONS

The Extended European Search Report in European Application No. 22202997.7 mailed on Apr. 4, 2023, 8 pages.
(Continued)

*Primary Examiner* — Benjamin L Lebron
*Assistant Examiner* — Eric J McCullough
(74) *Attorney, Agent, or Firm* — METIS IP LLC

(57) ABSTRACT

The embodiments of the disclosure provide a biological filtration system and a controlling method for the biological filtration system. The biological filtration system for filtering a solution in a bioreactor, comprises: a filter device having a top end and a bottom end, one of the top end and the bottom end being in fluid communication with the bioreactor for filtering the solution in the bioreactor; a liquid chamber in fluid communication with the other one of the top end and the bottom end for storing a solution in the filter device; a positive pressure pump, in fluid communication with the liquid chamber, for driving a solution to flow from the liquid chamber to the bioreactor; and a negative pressure pump, in fluid communication with the liquid chamber, for driving a solution to flow from the bioreactor to the liquid chamber.

18 Claims, 16 Drawing Sheets

10

10

(30) Foreign Application Priority Data

| | | |
|---|---|---|
| Oct. 21, 2021 | (CN) | 202122544496.7 |
| Oct. 21, 2021 | (CN) | 202122544497.1 |
| Oct. 21, 2021 | (CN) | 202122546148.3 |
| Oct. 11, 2022 | (CN) | 202222679392.1 |

(51) Int. Cl.

| | |
|---|---|
| ***B01D 35/147*** | (2006.01) |
| ***B01D 35/153*** | (2006.01) |
| ***B01D 36/00*** | (2006.01) |
| ***C12M 1/00*** | (2006.01) |
| ***C12M 1/34*** | (2006.01) |

(52) U.S. Cl.

CPC ......... *B01D 35/153* (2013.01); *B01D 36/001* (2013.01); *C12M 29/04* (2013.01); *C12M 41/44* (2013.01); *B01D 2201/167* (2013.01)

(56) References Cited

U.S. PATENT DOCUMENTS

| | | | | |
|---|---|---|---|---|
| 2010/0078395 | A1* | 4/2010 | Shevitz | B01D 35/30 210/455 |
| 2014/0120609 | A1* | 5/2014 | Goh | C12M 23/24 435/303.1 |
| 2014/0342446 | A1* | 11/2014 | Pralong | C12M 29/16 210/257.2 |
| 2014/0377739 | A1* | 12/2014 | Welch | C12Q 3/00 435/286.5 |
| 2015/0247114 | A1* | 9/2015 | Gebauer | C12M 41/00 435/243 |
| 2019/0040859 | A1 | 2/2019 | Pavlik | |
| 2019/0185803 | A1* | 6/2019 | Grant | C12M 41/48 |
| 2020/0181554 | A1 | 6/2020 | Grant | |
| 2020/0299636 | A1 | 9/2020 | Hazlebeck et al. | |
| 2021/0269477 | A1* | 9/2021 | Konstantinov | C12M 33/14 |
| 2021/0355430 | A1* | 11/2021 | Takahashi | C12M 29/00 |
| 2022/0186170 | A1 | 6/2022 | Liu et al. | |
| 2022/0186173 | A1 | 6/2022 | Liu et al. | |

FOREIGN PATENT DOCUMENTS

| | | | | |
|---|---|---|---|---|
| CN | 214032537 | U | 8/2021 | |
| CN | 113355242 | A | 9/2021 | |
| CN | 113457373 | A * | 10/2021 | C01B 13/0259 |
| JP | 2003325160 | A * | 11/2003 | C12M 41/14 |
| WO | 2009023562 | A2 | 2/2009 | |
| WO | WO-2020152509 | A1 * | 7/2020 | C12P 21/00 |

OTHER PUBLICATIONS

Li, Zujiang, Use and Maintenance of Medical Testing Instruments, People's Medical Publishing House Co., LTD., 1991, 2 pages.

First Office Action in Chinese Application No. 202111226940.9 mailed on Aug. 24, 2022, 35 pages.

* cited by examiner

10

700

BIOLOGICAL FILTRATION SYSTEMS AND CONTROLLING METHODS THEREOF

CROSS-REFERENCE TO RELATED APPLICATIONS

This application claims priority of Chinese Patent Application No. 202111226940.9, filed on Oct. 21, 2021, Chinese Patent Application No. 202122544210.5, filed on Oct. 21, 2021, Chinese Patent Application No. 202122544496.7, filed on Oct. 21, 2021, Chinese Patent Application No. 202122544497.1, filed on Oct. 21, 2021, Chinese Patent Application No. 202122546148.3, filed on Oct. 21, 2021, and Chinese Patent Application No. 202222679392.1, filed on Oct. 11, 2022, the entire contents of each of which are incorporated herein by reference.

TECHNICAL FIELD

The present disclosure generally relates to the field of biological filtration, and in particular, to a biological filtration system and a controlling method for the biological filtration system.

BACKGROUND

A biological filtration system refers to a system for processing or filtering biological solutions, which is usually used in filtration procedures such as replacing fresh culture medium, separating cell metabolites, and separating cells and culture medium. The main components of the biological filtration system include a filter device and a diaphragm pump. The filter device is used to communicate with the bioreactor. The diaphragm pump is disposed at the end of the filter device to provide a driving force for the filter device, and is used to drive the biological solution to flow circularly and flow back and forth between the filter device and the bioreactor, to achieve the goal of selective separation of components in the biological solution.

SUMMARY

One aspect of the present disclosure provides a biological filtration system. The biological filtration system includes a filter device having a top end and a bottom end, one of the top end and the bottom end being in fluid communication with the bioreactor for filtering the solution in the bioreactor; a liquid chamber in fluid communication with the other one of the top end and the bottom end for storing a solution in the filter device; a positive pressure pump, in fluid communication with the liquid chamber, for driving a solution to flow from the liquid chamber to the bioreactor; and a negative pressure pump, in fluid communication with the liquid chamber, for driving a solution to flow from the bioreactor to the liquid chamber.

In some embodiment, the filter device includes a filter portion and a storage portion, the filter portion is disposed close to the bottom end of the filter device, the storage portion is disposed close to the top end of the filter device, the storage portion is configured as a hollow chamber to form the liquid chamber, and the storage portion is in direct communication with the filter portion.

In some embodiments, the liquid chamber includes a single chamber that directly interfaces with the top end of the filter device.

In some embodiments, the liquid chamber comprises a single chamber connected to the top end or the bottom end of the filter device by a conduit.

In some embodiments, the liquid chamber comprises a plurality of chambers, and each of the chambers is connected to the top end or the bottom end of the filter device through a conduit.

In some embodiments, the biological filtration system includes a first conduit; the bottom end of the filter device is connected to the bioreactor through the first conduit; the positive pressure pump is used to drive the solution in the filter device to flow to the bioreactor along the first conduit; and the negative pressure pump is used to drive the solution in the bioreactor to flow to the filter device along the first conduit.

In some embodiments, the biological filtration system comprises a second conduit and a third conduit, and the bottom end of the filter device is connected to the bioreactor through the second conduit and the third conduit, the second conduit is disposed with a first one-way valve, so that the solution in the filter device flows to the bioreactor in one direction, the third conduit is disposed with a second one-way valve, so that the solution in the bioreactor flows to the filter device in one direction.

In some embodiments, the biological filtration system comprises a fourth conduit, a fifth conduit, and a sixth conduit, one of the top end and the bottom end of the filter device is connected to the chamber through the fourth conduit, the other one of the top end and the bottom end of the filter device is connected to the bioreactor through the fifth conduit, and the chamber is connected to the bioreactor through the sixth conduit, the positive pressure pump is used to drive the solution in the chamber to flow to the bioreactor through the filter device, and the negative pressure pump is used to drive the solution in the bioreactor to flow to the chamber; or the positive pressure pump is used to drive the solution in the chamber to flow to the bioreactor, and the negative pressure pump is used to drive the solution in the bioreactor to flow to the chamber through the filter device.

In some embodiments, the biological filtration system further comprises a first sensor and/or a negative pressure buffer chamber, wherein the first sensor is configured to detect liquid level information in the liquid chamber and is disposed on a top portion of the liquid chamber at a preset interval, and the negative pressure buffer chamber is disposed on a flow path between the negative pressure pump and the liquid chamber; and a second sensor, configured to detect the liquid level information in the liquid chamber and disposed on a bottom portion of the liquid chamber.

In some embodiments, the biological filtration system further comprises a third sensor and a fourth sensor for detecting liquid level information in the filter device, the filter device includes a reaction liquid port and a retentate liquid port, the third sensor is disposed at the reaction liquid port, and the fourth sensor is disposed at the retentate liquid port.

In some embodiments, the biological filtration system further comprises a gas purifier, the gas purifier is disposed on a flow path connecting the positive pressure pump and the negative pressure pump in the liquid chamber.

In some embodiments, the biological filtration system further comprises a cooling device, the cooling device is disposed for the liquid chamber, and is used to cool the air entering the gas purifier.

In some embodiments, the biological filtration system further comprises a liquid storage box, the liquid storage box is disposed on a flow path between the gas purifier and the negative pressure pump, and the liquid storage box is used to collect condensed water.

In some embodiments, the biological filtration system further comprises a check valve, the check valve is disposed on a flow path between the gas purifier and the negative pressure pump, and is used to prevent the condensed water from flowing back into the gas purifier.

In some embodiments, the biological filtration system further comprises a heating device, and the heating device is disposed for the gas purifier and/or the liquid chamber.

In some embodiments, the biological filtration system further comprises a first pressure regulating device and a second pressure regulating device, the first pressure regulating device is disposed at an outlet of the positive pressure pump and used to adjust a pumping gas pressure of the positive pressure pump, and the second pressure regulating device is disposed at an outlet of the negative pressure pump and used to adjust a suction gas pressure of the negative pressure pump.

In some embodiments, the biological filtration system further comprises a pressure relief bypass, the pressure relief bypass is disposed on a flow path between the liquid chamber and the positive pressure pump and/or the negative pressure pump for releasing gas pressure in the biological filtration system.

In some embodiments, the filter device is disposed with a penetrating liquid port, the biological filtration system further comprises a collection container and a flow controlling device, the penetrating liquid port is connected to the collection container, the flow controlling device is disposed between the collection container and the filter device, and the flow controlling device is used to control a flow rate of the solution in the filter device to the collection container.

In some embodiments, the biological filtration system further includes at least one pressure sensor for detecting the pressure signal of the solution and/or gas; the pressure sensor is disposed on the flow path between the filter device and the liquid chamber and/or, the pressure sensor is disposed on the flow path between the liquid chamber and the positive pressure pump and/or the negative pressure pump; and/or, the pressure sensor is disposed on the flow path between the filter device and the bioreactor.

In some embodiments, the biological filtration system further includes a processor configured to: obtain a first liquid level signal in the filter device or the liquid chamber; control the positive pressure pump to drive the solution in the filter device to flow to the bioreactor based on the first liquid level signal; obtain a second liquid level signal in the filter device or the liquid chamber; and control the negative pressure pump to drive the solution in the bioreactor to flow to the filter device based on the second liquid level signal.

In some embodiments, the processor is further configured to: obtain a first time of triggering the first liquid level signal; obtain a second time of triggering the second liquid level signal; based on a time difference between the first time and the second time, adjust the flow rate of the solution.

In some embodiments, the processor adjusts the flow rate of the solution based on the time difference between the first time and the second time, including: comparing the time difference with a preset time difference; if the time difference is less than the preset time difference, controlling the pressure regulating device of the biological filtration system to reduce pressure to reduce the flow rate of the solution; if the time difference is greater than the preset time difference, controlling the pressure regulating device to increase the pressure to increase the flow rate of the solution.

In some embodiments, the processor is further configured to: monitor the pressure signal in the biological filtration system; compare the pressure signal with a preset pressure threshold to determine whether there is a blockage in the biological filtration system; if there is a blockage, then send an alarm message.

Other aspect of the present disclosure provides a controlling method for a biological filtration system. The controlling method comprises: obtaining a first liquid level signal in the filter device or the liquid chamber; controlling the positive pressure pump to drive the solution in the filter device to flow to the bioreactor based on the first liquid level signal; obtaining a second liquid level signal in the filter device or the liquid chamber; and controlling the negative pressure pump to drive the solution in the bioreactor to flow to the filter device based on the second liquid level signal.

In some embodiments, the controlling method further comprises: obtaining a first time of triggering the first liquid level signal; obtaining a second time of triggering the second liquid level signal; based on a time difference between the first time and the second time, adjusting the flow rate of the solution.

In some embodiments, the based on a time difference between the first time and the second time, adjusting the flow rate of the solution comprises: comparing the time difference with a preset time difference; if the time difference is less than the preset time difference, controlling the pressure regulating device of the biological filtration system to reduce pressure to reduce the flow rate of the solution; if the time difference is greater than the preset time difference, controlling the pressure regulating device to increase the pressure to increase the flow rate of the solution.

In some embodiments, the controlling method further comprises: monitoring the pressure signal in the biological filtration system; comparing the pressure signal with a preset pressure threshold to determine whether there is a blockage in the biological filtration system; if there is a blockage, then sending an alarm message.

One aspect of the present disclosure provides a biological filtration system. The biological filtration system includes a filter device having a top end and a bottom end, one of the top end and the bottom end being in fluid communication with the bioreactor for filtering the solution in the bioreactor; a liquid chamber in fluid communication with the other one of the top end and the bottom end for storing a solution in the filter device; a positive pressure pump, in fluid communication with the liquid chamber, for driving a solution to flow from the liquid chamber to the bioreactor; and a negative pressure pump, in fluid communication with the liquid chamber, for driving a solution to flow from the bioreactor to the liquid chamber.

In some embodiments, the chamber of the liquid chamber directly interfaces with the top end of the filter device, or the chamber is connected to the filter device by a conduit.

In some embodiments, the biological filtration system includes a first conduit, the bottom end of the filter device is connected to the bioreactor through the first conduit, the positive pressure pump is used to drive the solution in the filter device to flow to the bioreactor along the first conduit, and the negative pressure pump is used to drive the solution in the bioreactor to flow to the filter device along the first conduit.

In some embodiments, the biological filtration system comprises a second conduit and a third conduit, and the bottom end of the filter device is connected to the bioreactor through the second conduit and the third conduit, the second conduit is disposed with a first one-way valve, so that the solution in the filter device flows to the bioreactor in one direction, the third conduit is disposed with a second one-way valve, so that the solution in the bioreactor flows to the filter device in one direction.

In some embodiments, the biological filtration system comprises a fourth conduit, a fifth conduit and a sixth conduit, one of the top end and the bottom end of the filter device is connected to the chamber through the fourth conduit, the other one of the top end and the bottom end of the filter device is connected to the bioreactor through the fifth conduit, and the chamber is connected to the bioreactor through the sixth conduit, the positive pressure pump is used to drive the solution in the chamber to flow to the bioreactor through the filter device, and the negative pressure pump is used to drive the solution in the bioreactor to flow to the chamber; or the positive pressure pump is used to drive the solution in the chamber to flow to the bioreactor, and the negative pressure pump is used to drive the solution in the bioreactor to flow to the chamber through the filter device.

In some embodiments, the biological filtration system further comprises a first sensor and a second sensor for detecting liquid level information in the liquid chamber, the first sensor is disposed on a top portion of at a preset interval, and the second sensor is disposed on a bottom portion of.

In some embodiments, the biological filtration system further comprises a third sensor and a fourth sensor for detecting liquid level information in the filter device, the filter device includes a reaction liquid port and a retentate liquid port, the third sensor is disposed at the reaction liquid port, and the fourth sensor is disposed at the retentate liquid port.

In some embodiments, the biological filtration system further comprises a first pressure regulating device and a second pressure regulating device, the first pressure regulating device is disposed at an outlet of the positive pressure pump and used to adjust a pumping gas pressure of the positive pressure pump, and the second pressure regulating device is disposed at an outlet of the negative pressure pump and used to adjust a suction gas pressure of the negative pressure pump.

In some embodiments, the biological filtration system further comprises a pressure relief bypass, the pressure relief bypass is disposed on a flow path between the liquid chamber and the positive pressure pump and/or the negative pressure pump for releasing gas pressure in the biological filtration system.

In some embodiments, the filter device is disposed with a penetrating liquid port, the biological filtration system further comprises a collection container and a flow controlling device, the penetrating liquid port is connected to the collection container, the flow controlling device is disposed between the collection container and the filter device, and the flow controlling device is used to control a flow rate of the solution in the filter device to the collection container.

In some embodiments, the biological filtration system further includes at least one pressure sensor for detecting the pressure signal of the solution and/or gas; the pressure sensor is disposed on the flow path between the filter device and the liquid chamber and/or, the pressure sensor is disposed on the flow path between the liquid chamber and the positive pressure pump and/or the negative pressure pump; and/or, the pressure sensor is disposed on the flow path between the filter device and the bioreactor.

In some embodiments, the biological filtration system further includes a processor configured to: obtain a first liquid level signal in the filter device or the liquid chamber; control the positive pressure pump to drive the solution in the filter device to flow to the bioreactor based on the first liquid level signal; obtain a second liquid level signal in the filter device or the liquid chamber; and control the negative pressure pump to drive the solution in the bioreactor to flow to the filter device based on the second liquid level signal.

In some embodiments, the processor is further configured to: obtain a first time of triggering the first liquid level signal; obtain a second time of triggering the second liquid level signal; based on a time difference between the first time and the second time, adjust the flow rate of the solution.

One aspect of the present disclosure provides a biological filtration system. The biological filtration system includes a filter device having a top end and a bottom end, one of the top end and the bottom end being in fluid communication with the bioreactor for filtering the solution in the bioreactor; a liquid chamber in fluid communication with the other one of the top end and the bottom end for storing a solution in the filter device; a positive pressure pump, in fluid communication with the liquid chamber, for driving a solution to flow from the liquid chamber to the bioreactor; and a negative pressure pump, in fluid communication with the liquid chamber, for driving a solution to flow from the bioreactor to the liquid chamber.

In some embodiments, the biological filtration system further comprises a first sensor and a second sensor for detecting liquid level information in the liquid chamber, the first sensor is disposed on a top portion of at a preset interval, and the second sensor is disposed on a bottom portion of.

In some embodiments, the biological filtration system further comprises a gas purifier, the gas purifier is disposed on a flow path connecting the positive pressure pump and the negative pressure pump in the liquid chamber.

In some embodiments, the biological filtration system further comprises a first pressure regulating device and a second pressure regulating device, the first pressure regulating device is disposed at an outlet of the positive pressure pump and used to adjust a pumping gas pressure of the positive pressure pump, and the second pressure regulating device is disposed at an outlet of the negative pressure pump and used to adjust a suction gas pressure of the negative pressure pump.

In some embodiments, the biological filtration system further comprises a pressure relief bypass, the pressure relief bypass is disposed on a flow path between the liquid chamber and the positive pressure pump and/or the negative pressure pump for releasing gas pressure in the biological filtration system.

In some embodiments, the filter device is disposed with a penetrating liquid port, the biological filtration system further comprises a collection container and a flow controlling device, the penetrating liquid port is connected to the collection container, the flow controlling device is disposed between the collection container and the filter device, and the flow controlling device is used to control a flow rate of the solution in the filter device to the collection container.

In some embodiments, the biological filtration system further includes at least one pressure sensor for detecting the pressure signal of the solution and/or gas; the pressure sensor is disposed on the flow path between the filter device and the liquid chamber and/or, the pressure sensor is disposed on the flow path between the liquid chamber and the positive pressure pump and/or the negative pressure pump; and/or, the pressure sensor is disposed on the flow path between the filter device and the bioreactor.

In some embodiments, the biological filtration system further includes a processor configured to: obtain a first liquid level signal in the filter device or the liquid chamber;

control the positive pressure pump to drive the solution in the filter device to flow to the bioreactor based on the first liquid level signal; obtain a second liquid level signal in the filter device or the liquid chamber; and control the negative pressure pump to drive the solution in the bioreactor to flow to the filter device based on the second liquid level signal.

In some embodiments, the processor is further configured to: obtain a first time of triggering the first liquid level signal; obtain a second time of triggering the second liquid level signal; based on a time difference between the first time and the second time, adjust the flow rate of the solution.

In some embodiments, the processor is further configured to: monitor the pressure signal in the biological filtration system; compare the pressure signal with a preset pressure threshold to determine whether there is a blockage in the biological filtration system; if there is a blockage, then send an alarm message.

One aspect of the present disclosure provides a biological filtration system. The biological filtration system includes a filter device having a top end and a bottom end, one of the top end and the bottom end being in fluid communication with the bioreactor for filtering the solution in the bioreactor; a liquid chamber in fluid communication with the other one of the top end and the bottom end for storing a solution in the filter device; a positive pressure pump, in fluid communication with the liquid chamber, for driving a solution to flow from the liquid chamber to the bioreactor; and a negative pressure pump, in fluid communication with the liquid chamber, for driving a solution to flow from the bioreactor to the liquid chamber; a liquid storage box, the liquid storage box is disposed on a flow path between the gas purifier and the negative pressure pump, and the liquid storage box is used to collect condensed water.

In some embodiments, the liquid storage box includes a top port and a bottom port, the top port is in fluid communication with the liquid chamber through the conduit, and the bottom port is in fluid communication with the negative pressure pump through the conduit.

In some embodiments, the biological filtration system further comprises a gas purifier, the gas purifier is disposed on a flow path connecting the positive pressure pump and the negative pressure pump in the liquid chamber.

In some embodiments, the biological filtration system further comprises a check valve, the check valve is disposed on a flow path between the gas purifier and the negative pressure pump, and is used to prevent the condensed water from flowing back into the gas purifier.

In some embodiments, the biological filtration system further comprises a cooling device, the cooling device is disposed for the liquid chamber, and is used to cool the air entering the gas purifier.

In some embodiments, the biological filtration system further comprises a heating device, and the heating device is disposed for the gas purifier and/or the liquid chamber.

In some embodiments, the liquid chamber includes a single chamber that directly interfaces with the top end of the filter device, or, the chamber is connected to the top end or the bottom end of the filter device by a conduit.

In some embodiments, the liquid chamber comprises a plurality of chambers, and each of the chambers is connected to the top end or the bottom end of the filter device through a conduit.

In some embodiments, the biological filtration system further comprises a first sensor and a second sensor for detecting liquid level information in the liquid chamber, the first sensor is disposed on a top portion of at a preset interval, and the second sensor is disposed on a bottom portion of.

In some embodiments, the biological filtration system further comprises a third sensor and a fourth sensor for detecting liquid level information in the filter device, the filter device includes a reaction liquid port and a retentate liquid port, the third sensor is disposed at the reaction liquid port, and the fourth sensor is disposed at the retentate liquid port.

In some embodiments, the biological filtration system further includes a processor configured to: obtain a first liquid level signal in the filter device or the liquid chamber; control the positive pressure pump to drive the solution in the filter device to flow to the bioreactor based on the first liquid level signal; obtain a second liquid level signal in the filter device or the liquid chamber; and control the negative pressure pump to drive the solution in the bioreactor to flow to the filter device based on the second liquid level signal.

In some embodiments, the processor is further configured to: obtain a first time of triggering the first liquid level signal; obtain a second time of triggering the second liquid level signal; based on a time difference between the first time and the second time, adjust the flow rate of the solution.

One aspect of the present disclosure provides a biological filtration system. The biological filtration system includes a filter device having a top end and a bottom end, and includes a filter portion and a storage portion, the filter portion is disposed close to the bottom end of the filter device, the storage portion is disposed close to the top end of the filter device, the storage portion is configured as a hollow chamber to form the liquid chamber, and the storage portion is in direct communication with the filter portion, to buffer the solution in the filter device; a positive pressure pump, in fluid communication with the storage portion, for driving a solution to flow from the storage portion to the bioreactor; and a negative pressure pump, in fluid communication with the storage portion, for driving a solution to flow from the bioreactor to the storage portion.

In some embodiments, the biological filtration system includes a first conduit, the bottom end of the filter device is connected to the bioreactor through the first conduit, the positive pressure pump is used to drive the solution in the filter device to flow to the bioreactor along the first conduit, and the negative pressure pump is used to drive the solution in the bioreactor to flow to the filter device along the first conduit.

In some embodiments, the biological filtration system comprises a second conduit and a third conduit, and the bottom end of the filter device is connected to the bioreactor through the second conduit and the third conduit, the second conduit is disposed with a first one-way valve, so that the solution in the filter device flows to the bioreactor in one direction, the third conduit is disposed with a second one-way valve, so that the solution in the bioreactor flows to the filter device in one direction.

In some embodiments, the biological filtration system further comprises a first sensor and a second sensor for detecting liquid level information in the storage portion, the first sensor is disposed on a top portion of the storage portion at a preset interval, and the second sensor is disposed on the bottom of the storage portion.

In some embodiments, the biological filtration system further comprises a gas purifier, the gas purifier is disposed on a flow path of the storage portion connecting the positive pressure pump and the negative pressure pump.

In some embodiments, the biological filtration system further comprises a heating device, and the heating device is disposed for the gas purifier and/or the storage portion.

In some embodiments, the biological filtration system further comprises a first pressure regulating device and a second pressure regulating device, the first pressure regulating device is disposed at an outlet of the positive pressure pump and used to adjust a pumping gas pressure of the positive pressure pump, and the second pressure regulating device is disposed at an outlet of the negative pressure pump and used to adjust a suction gas pressure of the negative pressure pump.

In some embodiments, the biological filtration system further comprises a pressure relief bypass, the pressure relief bypass is disposed on a flow path between the storage portion and the positive pressure pump and/or the negative pressure pump for releasing gas pressure in the biological filtration system.

In some embodiments, the filter device is disposed with a penetrating liquid port, the biological filtration system further comprises a collection container and a flow controlling device, the penetrating liquid port is connected to the collection container, the flow controlling device is disposed between the collection container and the filter device, and the flow controlling device is used to control a flow rate of the solution in the filter device to the collection container.

In some embodiments, the biological filtration system further includes a processor configured to: obtain a first liquid level signal in the filter device or the storage portion; control the positive pressure pump to drive the solution in the filter device to flow to the bioreactor based on the first liquid level signal; obtain a second liquid level signal in the filter device or the storage portion; and control the negative pressure pump to drive the solution in the bioreactor to flow to the filter device based on the second liquid level signal.

In some embodiments, the processor is further configured to: obtain a first time of triggering the first liquid level signal; obtain a second time of triggering the second liquid level signal; based on a time difference between the first time and the second time, adjust the flow rate of the solution.

One aspect of the present disclosure provides a biological filtration system. The biological filtration system includes a filter device having a top end and a bottom end, one of the top end and the bottom end being in fluid communication with the bioreactor for filtering the solution in the bioreactor; a liquid chamber in fluid communication with the other one of the top end and the bottom end for storing a solution in the filter device; a positive pressure pump, in fluid communication with the liquid chamber, for driving a solution to flow from the liquid chamber to the bioreactor; and a negative pressure pump, in fluid communication with the liquid chamber, for driving a solution to flow from the bioreactor to the liquid chamber, and a negative pressure buffer chamber is disposed on a flow path between the negative pressure pump and the liquid chamber.

In some embodiments, the biological filtration system further comprises a first sensor for detecting liquid level information in the liquid chamber, the first sensor is disposed on a top portion of at a preset interval.

In some embodiments, the biological filtration system does not include a first sensor, and the negative pressure buffer chamber is used to control the liquid level in the liquid chamber.

In some embodiments, a second pressure regulating device is disposed between the negative pressure pump and the negative pressure buffer chamber, and the second pressure regulating device is used to control the suction gas pressure of the negative pressure pump to the negative pressure buffer chamber.

In some embodiments, a load cell is disposed in the negative pressure buffer chamber or between the negative pressure buffer chamber and the negative pressure pump, and the load cell is used to detect the pressure in the negative pressure buffer chamber.

In some embodiments, the liquid chamber comprises a single chamber connected to the top end or the bottom end of the filter device by a conduit.

In some embodiments, the liquid chamber comprises a plurality of chambers, and each of the chambers is connected to the top end or the bottom end of the filter device through a conduit.

In some embodiments, a throttle valve is further disposed between the negative pressure buffer chamber and the liquid chamber, and the throttle valve is used to control the flow rate of the solution in the liquid chamber to the negative pressure buffer chamber.

In some embodiments, a flow sensor is disposed between the bioreactor and the liquid chamber, and the flow sensor is used to collect a flow signal of the solution of the bioreactor flowing to the liquid chamber.

In some embodiments, the biological filtration system further includes a processor; when the biological filtration system comprises a first sensor, the first sensor is signal-connected to the processor; when the biological filtration system includes a second pressure regulating device, the second pressure regulating device is signal-connected to the processor; when the biological filtration system includes a load cell, the load cell is signal-connected to the processor; when the biological filtration system includes a throttle valve, the throttle valve is signal-connected to the processor; when the biological filtration system includes a flow sensor, the flow sensor is signal-connected to the processor.

BRIEF DESCRIPTION OF THE DRAWINGS

The present disclosure is further illustrated in terms of exemplary embodiments. These exemplary embodiments are described in detail with reference to the drawings. These embodiments are not restrictive. In these embodiments, the same number indicates the same structure, wherein.

Figure 1A:
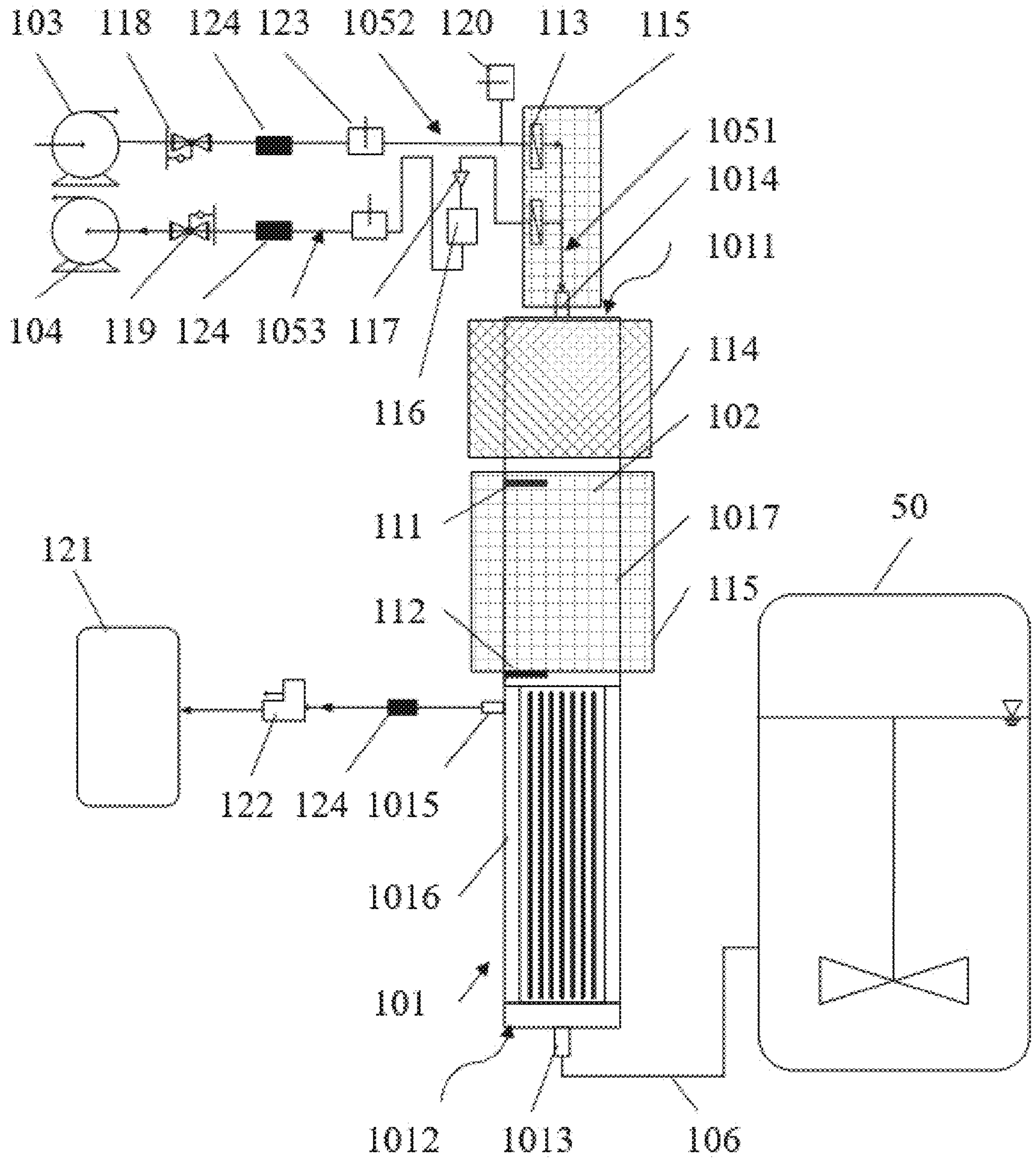
FIG. 1A is a schematic diagram illustrating an exemplary biological filtration system according to embodiment 1 of the present disclosure.

In the figures, 10, 20, 30, and 40 are biological filtration systems; 50 is a bioreactor; 101 is a filter device; 1011 is a top end; 1012 is a bottom end; 1013 is a reaction liquid port; 1014 is a retentate liquid port; 1015 is a penetrating liquid port; 1016 is a filter portion; 1017 is a storage portion; 102, 202, 302, 402 are liquid chambers; 103 is a positive pressure pump; 104 is a negative pressure pump; 1051 is a circuit; 1052 is a positive pressure branch; 1053 is a negative pressure branch; 106 is a first conduit; 107 is a second conduit; 108 is a third conduit; 125 is a fourth conduit; 126 is a fifth conduit; 127 is a sixth conduit; 1054 is a first multiway conduit; 1055 is a second multiway conduit; 109 is a first one-way valve; 110 is a second one-way valve; 111 is a first sensor; 112 is a second sensor; 203 is a third sensor; 204 is a fourth sensor; 113 is a gas purifier; 114 is a cooling device; 115 is a heating device; 116 is a liquid storage box; 117 is a check valve; 118 is a first pressure regulating device; 119 is a second pressure regulating device; 120 is a pressure relief bypass; 121 is a collection container; 122 is a flow controlling device; 123 is a solenoid valve; 124 is a pressure sensor; 130 is a negative pressure buffer chamber; 140 is a flow sensor; 900 is a processing device; 910 is a storage medium; and 920 is a processor.

DETAILED DESCRIPTION

In the following detailed description, numerous specific details are set forth by way of examples in order to provide a thorough understanding of the relevant disclosure. Obviously, drawings described below are only some examples or embodiments of the present disclosure. Those skilled in the art, without further creative efforts, may apply the present disclosure to other similar scenarios according to these drawings. It should be understood that the purposes of these illustrated embodiments are only provided to those skilled in the art to practice the application, and not intended to limit the scope of the present disclosure. Unless obviously obtained from the context or the context illustrates otherwise, the same numeral in the drawings refers to the same structure or operation.

It will be understood that the terms "system," "engine," "unit," "module," and/or "block" used herein are one method to distinguish different components, elements, parts, sections, or assemblies of different levels in ascending order. However, the terms may be displaced by other expressions if they may achieve the same purpose.

The terminology used herein is for the purposes of describing particular examples and embodiments only and is not intended to be limiting. As used herein, the singular forms "a," "an," and "the" may be intended to include the plural forms as well, unless the context clearly indicates otherwise. It will be further understood that the terms "include" and/or "comprise," when used in this disclosure, specify the presence of integers, devices, behaviors, stated features, steps, elements, operations, and/or components, but do not exclude the presence or addition of one or more other integers, devices, behaviors, features, steps, elements, operations, components, and/or groups thereof.

Although the present disclosure makes various references to certain modules or units in systems according to embodiments of the present disclosure, any number of different modules or units may be used and run on the client and/or server superior. The modules are illustrative only, and different aspects of the systems and methods may use different modules.

The flowcharts used in the present disclosure illustrate operations that systems implement according to some embodiments of the present disclosure. It is to be expressly understood, the operations of the flowcharts may be implemented not in order. Conversely, the operations may be implemented in an inverted order, or simultaneously. Moreover, one or more other operations may be added to the flowcharts. One or more operations may be removed from the flowcharts.

In related fields such as cell culture, the biological filtration system filters the reaction solution in the bioreactor based on physical and/or chemical properties to obtain the desired culture solution. In some embodiments of the present disclosure, the biological filtration system may filter the reaction liquid in the bioreactor, and the reaction liquid refers to the solution that needs to be filtered. The filtered solution includes retentate liquid and penetrating liquid. The retentate liquid refers to the solution that is blocked by the filter device in the biological filtration system, which may then be re-entered into the bioreactor for re-filtration. The penetrating liquid refers to the solution that passes through the filter device in the biological filtration system. The retentate liquid may be the desired culture solution and the penetrating liquid may be the waste solution, or the retentate liquid may be the waste solution and the penetrating may be the desired culture solution. In some embodiments, the retentate liquid in the biological filtration system may be re-drained into the bioreactor to form a new reaction liquid. To simplify the description, the reaction liquid, the retentate liquid and the penetrating liquid are collectively referred to as solutions in the present disclosure.

In some embodiments, the filter device and the liquid chamber are integrally formed, the filter device includes a filter portion and a storage portion, the liquid chamber is integrated in the storage portion and directly connected to the filter portion, so that the integrated design of the liquid chamber inside the filter device makes the design more compact, which not only simplifies the structure of the biological filtration system, but also reduces the volume of space occupied by the filter device and the liquid chamber. In some embodiments, the liquid chamber includes a single chamber that is directly connected to the top end of the filter device, which can reduce the amount of solution circulating outside the bioreactor and filter device. In some embodiments, the liquid chamber includes a single chamber, and the chamber is connected to the top end or bottom end of the filter device through a conduit, which can increase the flexibility of the arrangement position of the liquid chamber. In some embodiments, the liquid chamber and the filter device are arranged separately and includes a plurality of chambers, each chamber is in fluid communication with the positive pressure pump and the negative pressure pump, and each chamber is in communication with the filter device, so that the positive pressure pump delivers positive pressure to part of the chambers, while the negative pressure pump delivers negative pressure to another part of the chambers to improve the filtration efficiency of the solution between the filter device and the bioreactor. In some embodiments, multiple biological filtration systems may be connected to the same bioreactor to improve the filtration efficiency of the solution in the bioreactor.

Figure 1B:
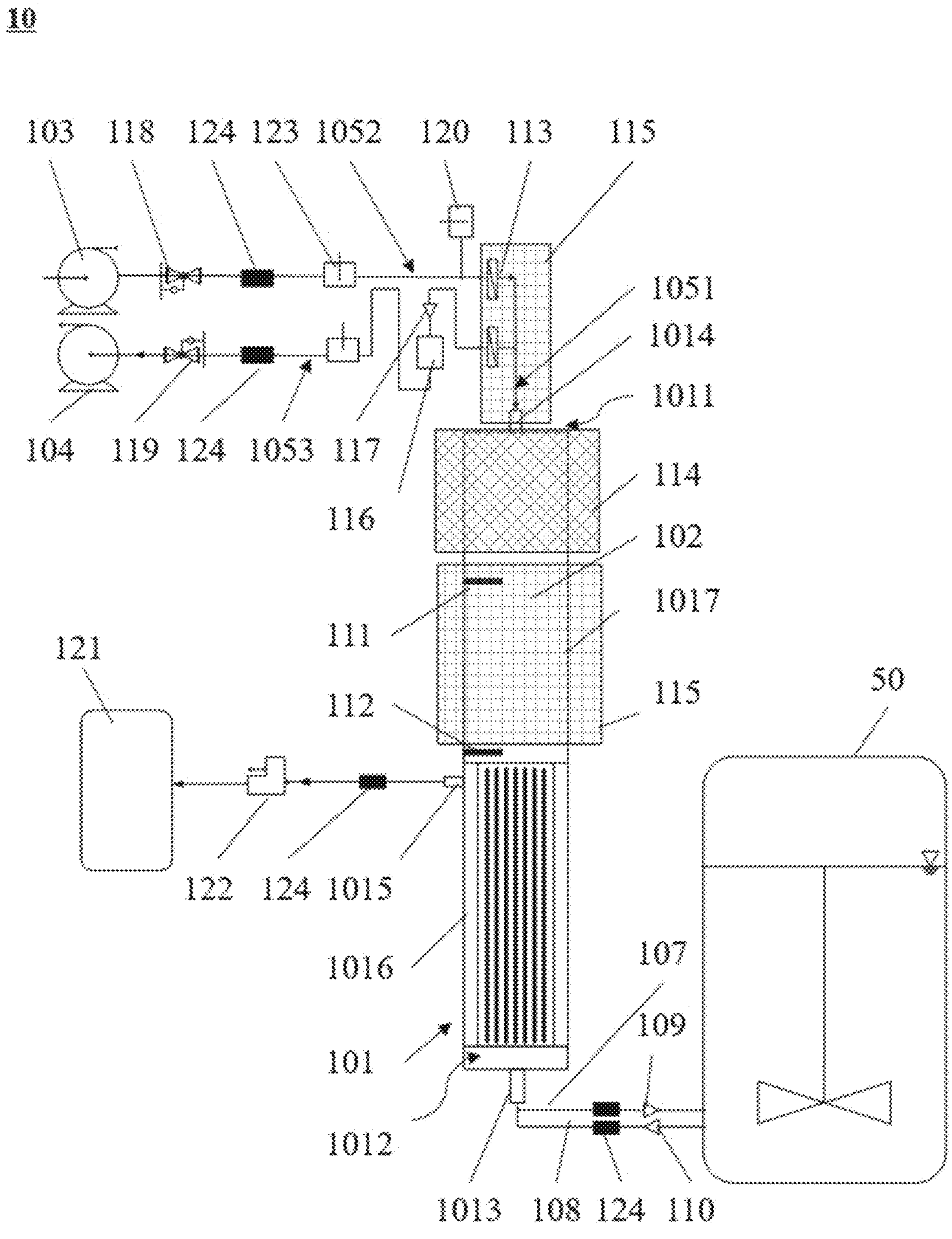
FIG. 1B is a schematic diagram illustrating an exemplary biological filtration system according to embodiment 1 of the present disclosure.

FIG. 1A and FIG. 1B are schematic diagrams illustrating an exemplary biological filtration system according to embodiment 1 of the present disclosure.

Referring to FIG. 1A and FIG. 1B, embodiment 1 of the present disclosure provides a biological filtration system 10, the biological filtration system 10 is used to connect a bioreactor 50 and drive the solution in the bioreactor 50 to flow circularly/back and forth between the biological filtration system 10 and the bioreactor 50 to filter the solution in the bioreactor 50. In some embodiments, the bioreactor 50 may be a vessel for holding or processing the reaction liquid that needs to be filtered.

In embodiment 1, the biological filtration system 10 may include components such as a filter device 101, a liquid chamber 102, a positive pressure pump 103 and a negative pressure pump 104.

In some embodiments, the filter device 101 refers to a device capable of selective separation based on the physical and/or chemical properties of certain components in the solution, for example, the filter device 101 may be a biofilm filter device 101, a hollow fiber column filter device 101 and other various types of filter device s 101, which are not limited in the present disclosure. In some embodiments, the filter device 101 has a top end 1011 and a bottom end 1012, wherein the top end 1011 and the bottom end 1012 are defined based on the orientation in which the filter device 101 is conventionally used, for example, the filter device 101 is generally placed vertically, the top end 1011 may be an upper end and bottom end 1012 of the filter device 101 may be a lower end of the filter device 101, but the filter device 101 may also be placed in any suitable orientation, and the top end 1011 and the bottom end 1012 may also be adaptively rotated and adjusted according to the orientation of the filter device 101.

In some embodiments, the filter device 101 may include a reaction liquid port 1013, a retentate liquid port 1014 and a penetrating liquid port 1015. The reaction liquid enters the filter device 101 from the reaction liquid port 1013, and is filtered inside the filter device 101 to form retentate liquid and penetrating liquid. The retentate liquid exits the filter device 101 from the retentate liquid port 1014 or the retentate liquid returns to the reaction liquid port 1013 to exit the filter device 101, and the penetrating liquid exits the filter device 101 from the penetrating liquid port 1015. In some embodiments, the reaction liquid port 1013 may be located at the bottom end 1012 of the filter device 101, the retentate liquid port 1014 may be located at the top end 1011 of the filter device 101, and the penetrating liquid port 1015 may be located at a side of the filter device 101.

In embodiment 1, the bottom end 1012 of the filter device 101 is used to be in fluid communication with the bioreactor 50, and further, the reaction liquid port 1013 of the bottom end 1012 of the filter device 101 is in fluid communication with the bioreactor 50, so that the solution in the bioreactor 50 may flow into the filter device 101 from the reaction liquid port 1013. Fluid communication refers to a connection or link that allows fluid to flow between the filter device 101 and the bioreactor 50, including but not limited to connection forms such as conduit connection, interface connection, or direct connection. The fluid communication referred to hereinafter in the present disclosure is similar to the definition here, and will not be repeated here.

In some embodiments, the liquid chamber 102 may be a container for storing the solution, or may be a chamber that provides a buffer space for the solution flowing out of the filter device 101. In some embodiments, the liquid chamber 102 may be integrated with the filter device 101 as a single structure, for example, referring to the biological filtration system 10 provided in embodiment 1. In some embodiments, the liquid chamber 102 may be designed separately from the filter device 101, for example, referring to the biological filtration system 10 provided in embodiments 2 to 4.

In embodiment 1, the liquid chamber 102 may be integrated with the filter device 101 as an integral structure. In some embodiments, the filter device 101 includes a filter portion 1016 and a storage portion 1017. The filter portion 1016 may be close to the end where the reaction liquid port 1013 is located, that is, the filter portion 1016 may be close to the bottom end 1012 of the filter device 101. The buffer part 1017 may be close to the end where the retentate liquid port 1014 is located, that is, the storage portion 1017 may be close to the top end 1011 of the filter device 101. In some embodiments, the filter portion 1016 is provided with filter elements such as filter membranes or hollow fiber columns. In some embodiments, the storage portion 1017 is configured as a hollow chamber to form the liquid chamber 102, that is, the liquid chamber 102 and the storage portion 1017 are integrated into a single structure. In some embodiments, in the height direction of the filter device 101, the ratio of the height of the storage portion 1017 to the height of the filter portion 1016 may be ½, ⅔, ¾, etc., which is not limited in the present disclosure.

In some embodiments, the storage portion 1017 is directly communicated with the filter portion 1016, that is, the storage portion 1017 and filter portion 1016 are arranged adjacently and are not communicated by other elements, and an outlet of the filter element may be the entrance of the storage portion 1017. In some embodiments, the storage portion 1017 and the filter portion 1016 may be an integrally formed structure separated from each other by a spacer in the middle. In some embodiments, the storage portion 1017 may buffer the solution, that is, after the solution in the filter portion 1016 enters the storage portion 1017, the solution may return to the bottom of the storage portion 1017 and enter the filter portion 1016 after the storage portion 1017 accumulates to a certain volume, and then the solution is discharged from the filter device 101 from the bottom of the filter portion 1016. In some embodiments, the storage portion 1017 may provide a buffer space for the solution, that is, after the solution reaches the top of the filter element, the solution reaches the top of the filter portion 1016 and then enters the storage portion 1017, and the storage portion 1017 may prevent the solution from flowing into other components (e.g., a gas purifier 113 mentioned below), and the solution may be completely immersed in the filter portion 1016, so that the filtration is more sufficient.

The integrated design of the liquid chamber 102 inside the filter device 101 makes the design more compact, which may not only simplify the structure of the biological filtration system 10, but also reduce the volume of space occupied by the filter device 101 and the liquid chamber 102. In addition, the liquid chamber 102 is in direct communication with the filter portion 1016, and the solution flows into the liquid chamber 102 without obstacles after passing through the filter portion 1016, which reduces the resistance of the fluid and helps reduce the power loss of the biological filtration system 10.

In some embodiments, the power of the biological filtration system 10 may be provided by a positive pressure pump 103 and a negative pressure pump 104. The positive pressure pump 103 is in fluid communication with the liquid chamber 102 (i.e., the storage portion 1017), for example, through a fluid communication manner such as conduit communication. In some embodiments, the positive pressure pump 103 may pump gas to the liquid chamber 102, and provide positive pressure to the solution in the liquid chamber 102 by pumping the gas, thereby driving the solution to flow from the liquid chamber 102 to the bioreactor 50.

In some embodiments, the negative pressure pump 104 is in fluid communication with the liquid chamber 102 (i.e., the storage portion 1017), for example, through a fluid communication manner such as conduit communication. In some embodiments, the negative pressure pump 104 may suck out the gas in the liquid chamber 102, and provide negative pressure to the solution in the liquid chamber 102 by sucking the gas, thereby driving the solution to flow from the bioreactor 50 to the liquid chamber 102.

In embodiment 1, the retentate liquid port 1014 at the top of the filter device 101 is connected to the storage portion 1017, and the positive pressure pump 103 and the negative pressure pump 104 may be connected to the retentate liquid port 1014 through a three-way conduit. In some embodiments, the three-way conduit includes a circuit 1051, a positive pressure branch 1052, and a negative pressure branch 1053, one end of the circuit 1051 is connected to the retentate liquid port 1014, and one end of the positive pressure branch 1052 is connected to the positive pressure pump 103, and one end of the negative pressure branch 1053 is connected to the negative pressure pump 104.

In some embodiments, the positive pressure pump 103 and the negative pressure pump 104 may be independently controlled according to specific conditions of use. For example, in some application scenarios, the solution needs to flow slowly from the bioreactor 50 to the filter device 101, and then the solution needs to flow rapidly from the filter device 101 to the bioreactor 50, the powers of the positive pressure pump 103 and the negative pressure pump 104 may be set independently according to different pressure values provided to the liquid chamber 102 at different stages. For another example, in some application scenarios, for a biological filtration system with multiple chambers (for details, refer to embodiment 4), for a chamber that requires positive pressure and a chamber that requires negative pressure, the powers of the positive pressure pump 103 and the negative pressure pump 104 may be set separately according to requirements to provide different pressure values for different chambers. Positive pressure and negative pressure are respectively applied to the liquid chamber 102 by setting the positive pressure pump 103 and the negative pressure pump 104 to drive the flow of the solution between the biological filtration system 10 and the bioreactor 50, the positive pressure pump 103 and the negative pressure pump 104 do not affect each other during operation, and the operation time and power of the two may be controlled independently, which improves the control flexibility. In addition, the negative pressure pump 103 and the positive pressure pump 104 are used as power sources, which may quickly build up pressure in the liquid chamber, and the pressure is stable.

In some embodiments, the communication between the filter device 101 and the bioreactor 50 may be through a conduit. In embodiment 1, the reaction liquid port 1013 of the bottom end 1012 of the filter device 101 is communicated with the bioreactor 50 through a conduit, and the filter device 101 may be communicated with the bioreactor 50 through one conduit, or may be communicated with the bioreactor 50 through two conduits.

In some embodiments, referring to FIG. 1A, the biological filtration system 10 may include a first conduit 106 through which the bottom end 1012 of the filter device 101 is connected to the bioreactor 50. In some embodiments, when the positive pressure pump 103 is running, the solution in the filter device 101 may flow to the bioreactor 50 along the first conduit 106, and when the negative pressure pump 104 is running, the solution in the bioreactor 50 may flow to the filter device 101 along the first conduit 106, that is, the solution flows back and forth along the first conduit 106.

In some embodiments, referring to FIG. 1B, the biological filtration system 10 may include a second conduit 107 and a third conduit 108 through which the bottom end 1012 of the filter device 101 is connected to the bioreactor 50. In some embodiments, when the positive pressure pump 103 is running, the solution in the filter device 101 may flow to the bioreactor 50 along the second conduit 107, and when the negative pressure pump 104 is running, the solution in the bioreactor 50 may flow to the filter device 101 along the third conduit 108, that is, the solution flows circularly along the second conduit 107 and the third conduit 108.

In some embodiments, the second conduit 107 is provided with a first one-way valve 109, so that the solution in the filter device 101 (through the second conduit 107) flows to the bioreactor 50 in one direction, and the third conduit 108 is provided with a second one-way valve 110, so that the solution in the bioreactor 50 (through the third conduit 108) flows to the filter device 101 in one direction. In this way, the first one-way valve 109 and the second one-way valve 110 may control a circulation flow direction of the solution, and the controller does not need to participate in the control of the flow direction of the solution, which simplifies the control strategy.

In some embodiments, the liquid chamber 102 may be a container for storing the solution, and the biological filtration system 10 further includes a first sensor 111 and a second sensor 112 for detecting liquid level information in the liquid chamber 102, to facilitate the determination of the amount of the solution in the liquid chamber 102. In some embodiments, the liquid level information may be the height position information of the solution in the liquid chamber 102. In some embodiments, the first sensor 111 and the second sensor 112 include, but are not limited to, various types of sensors such as a contact liquid level sensor and a non-contact liquid level sensor.

In some embodiments, the first sensor 111 may be disposed on a top portion of 102 at a preset interval, and the position of the first sensor 111 is used to determine the allowable high liquid level line in the liquid chamber 102. The preset interval refers to the height distance from the first sensor 111 to the top of the liquid chamber 102, for example, the preset interval may be ½, ⅓ or ¼ of the entire height of the liquid chamber 102, etc., and there is no restriction here. In some embodiments, a space between the first sensor 111 and the top of the liquid chamber 102 may provide a buffer for the solution to prevent the solution from overflowing from the top of the liquid chamber 102 to the positive pressure branch 1052 and the negative pressure branch 1053.

In some embodiments, the second sensor 112 is disposed at the bottom of the liquid chamber 102, and the location of the second sensor 112 is used to determine the allowable low liquid level line in the liquid chamber 102. In embodiment 1, the second sensor 112 may be disposed close to the upper surface of the filter element of the filter device 101. In embodiments 3 and 4, the second sensor 112 may be disposed at the bottom of the inner side of the liquid chamber 102. By setting the second sensor 112, the positive pressure pump 103 may be controlled to stop running in time when the solution reaches the lowest position of the liquid chamber 102, which may prevent gas or bubbles from entering the filter portion 1016 of the filter device 101 and affecting the filtration effect of the filter device 101.

In embodiment 1, under the action of negative pressure pump 104, the solution in the bioreactor 50 gradually flows into the filter device 101, and the solution level in the liquid chamber 102 gradually rises until the first sensor 111 detects that when a liquid level signal is present, it means that the solution reaches the high liquid level line, and the operation of the negative pressure pump 104 is stopped at this time. In some embodiments, under the action of the positive pressure pump 103, the solution in the filter device 101 gradually flows into the bioreactor 50, and the liquid level of the solution in the liquid chamber 102 gradually decreases until the second sensor 112 detects that when a liquid level signal is present, it means that the solution reaches the low liquid level line, and the operation of the positive pressure pump 103 is stopped at this time. The operation strategy of the positive pressure pump 103 and the negative pressure pump 104 may be more precisely controlled by the first sensor 111 and the second sensor 112, thereby improving the efficiency of the circulation/reciprocating flow of the solution between the filter device 101 and the bioreactor 50.

In some embodiments, the biological filtration system 10 also includes a gas purifier 113 for filtering the gas entering and exiting the liquid chamber 102. In some embodiments, the gas purifier 113 may be a sterile filter, which mainly filters pollutants such as impurities and bacteria in the gas. In some embodiments, the gas pumped by the positive pressure pump 103 flows through the gas purifier 113 and then enters the liquid chamber 102 to prevent contamination of the solution in the liquid chamber 102; the gas pumped by the negative pressure pump 104 from the liquid chamber 102 passes through the gas filter may purify the gas in the negative pressure branch 1053, so that when the positive pressure pump 103 is working, even if the residual gas in the negative pressure branch 1053 returns to the liquid chamber 102, it will not pollute the solution.

In some embodiments, there are two gas purifiers 113, one gas purifier 113 is disposed on the positive pressure branch 1052 connected to the positive pressure pump 103, and the other gas purifier 113 is disposed on the negative pressure branch 1053 connected to the negative pressure pump 104. In some embodiments, there is one gas purifier 113, and the gas purifier 113 is disposed on the circuit 1051 connecting the liquid chamber 102.

In some embodiments, the solution in the bioreactor 50 and the filter device 101 generally need to be maintained within a constant temperature range, for example, some biological cell reaction solutions may be maintained at around 37° C. The gas in the liquid chamber 102 contains a large amount of moisture at a relatively high temperature, and the gas with a large amount of moisture tends to wet the filter element of the gas purifier 113 when passing through the gas purifier 113, and causes the gas purifier 113 to fail. Based on this, in some embodiments, the biological filtration system 10 further includes a cooling device 114, the cooling device 114 may be disposed for the liquid chamber 102 for cooling the gas entering the gas purifier 113, so that the moisture in the gas is partially condensed into condensed water to reduce the moisture content of the gas.

In embodiment 1, the cooling device 114 may be disposed on the outer surface of the storage portion, and disposed in the area between the first sensor 111 and the top of the liquid chamber 102. In some embodiments, the cooling device 114 may be a heat sink or a condensing fin, and the heat sink or the condensing fin may accelerate the heat exchange between the gas and the outside, so that part of the moisture in the gas condenses into condensed water and returns to the solution in the liquid chamber 102.

In some embodiments, the biological filtration system 10 further includes a heating device 115, and the heating device 115 is disposed for the gas purifier 113 and/or the liquid chamber 102. In some embodiments, the heating device 115 is disposed for the gas purifier 113 to prevent moisture in the gas in the gas purifier 113 from condensing and wetting the filter element. In some embodiments, the heating device 115 is disposed for the liquid chamber 102, for example, the heating device 115 may be disposed for the part of the liquid chamber 102 located between the first sensor 111 and the second sensor 112, for maintaining the temperature of the solution inside of the liquid chamber 102. In some embodiments, the heating device 115 is provided corresponding to both the gas purifier 113 and the liquid chamber 102.

In some embodiments, only the heating device 115 may be provided outside the liquid chamber 102 without the condensation device, in other words, the heating device 115 may be provided corresponding to the entire liquid chamber 102. In some embodiments, there may be one heating device 115, and the liquid chamber 102 and the gas purifier 113 are simultaneously within the heat radiation range of the same heating device 115.

In some embodiments, the cooling device 114 is provided at the liquid chamber 102, and the heating device 115 is provided at the gas purifier 113, the cooling device 114 first cools the gas in the liquid chamber 102, so that the humidity of the gas is increased or even saturated to precipitate condensate water, thereby reducing the moisture content in the gas. Next, after the gas enters the gas purifier 113, the heating device 115 heats the gas to reduce the humidity of the gas to avoid wetting the filter element of the gas purifier 113.

In some embodiments, the heating device 115 may be a warm air device capable of blowing hot air toward the gas purifier 113 and/or the liquid chamber 102. In some embodiments, the heating device 115 may be a heating wire, and the heating wire is coated on the outer surface of the gas purifier 113 and/or the liquid chamber 102 by a thermal insulation medium (such as thermal insulation cotton, thermal insulation foam, etc.), providing heat for the gas purifier 113 and/or the liquid chamber 102.

In some embodiments, the biological filtration system 10 further includes a liquid storage box 116, the liquid storage box 116 is disposed on the flow path between the gas purifier 113 and the negative pressure pump 104, and the liquid storage box 116 is used to collect the condensed water. In some embodiments, the gas flowing out of the gas purifier 113 is cooled in the conduit to form condensed water, and the liquid storage box 116 may collect the condensed water and collect the condensed water at the bottom of the liquid storage box 116, preventing the condensed water from flowing back into the gas purifier 113.

In some embodiments, the liquid storage box 116 includes a top port and a bottom port, the top port is in fluid communication with the liquid chamber 102 through the conduit, and the bottom port is in fluid communication with the negative pressure pump 104 through the conduit. In some embodiments, the negative pressure branch 1053 is not provided with an air purifier, and the top port of the liquid storage box 116 is in direct communication with the liquid chamber 102. In some embodiments, an air purifier is further disposed between the top port of the liquid storage box 116 and the liquid chamber 102, and the top port of the liquid storage box 116 communicates with the liquid chamber 102 through the air purifier. The condensed water enters the liquid storage box 116 from the top port and collects at the bottom of the liquid storage box 116, and the condensed water is continuously pumped to the outside for discharge under the action of the negative pressure pump 104 to prevent the condensed water from accumulating in the liquid storage box 116.

In some embodiments, the heating device 115 may also be provided corresponding to the liquid storage box 116, and the negative pressure pump 104 may suck most of the condensed water to the outside. When the negative pressure pump 104 stops working, the heating device 115 may heat the remaining condensed water and gas in the liquid storage box 116 to maintain a high temperature state to prevent the precipitation of condensed water from the gas, thereby reducing the amount of condensed water. In some embodiments, the liquid storage box 116, the gas purifier 113 and the liquid chamber 102 may be simultaneously within the heat radiation range of the same heating device 115. In some embodiments, the liquid storage box 116 and the gas purifier 113 are simultaneously within the heat radiation range of the same heating device 115, and the liquid chamber 102 corresponding to the part between the first sensor 111 and the second sensor 112 is within another heat radiation range of the heating device 115, the part between the top of the liquid chamber 102 and the first sensor 111 is within the radiation range of the cooling device 114.

In some embodiments, the biological filtration system 10 further includes a check valve 117, which is disposed on the flow path between the gas purifier 113 and the negative pressure pump 104. The check valve 117 allows fluids such as gas and condensed water to flow in one direction from the gas purifier 113 to the negative pressure pump 104 to prevent the condensed water from flowing back into the gas purifier 113. In some embodiments, the check valve 117 may be provided between the gas purifier 113 and the liquid storage box 116. In some embodiments, the check valve 117 may be provided between the liquid storage box 116 and the negative pressure pump 104.

In some embodiments, the biological filtration system 10 further includes a first pressure regulating device 118 and a second pressure regulating device 119. The rate at which the solution flows between the liquid chamber 102 and the bioreactor 50 may be controlled by the first pressure regulating device 118 and the second pressure regulating device 119.

In some embodiments, the first pressure regulating device 118 is disposed at an outlet of the positive pressure pump 103 for regulating the pumping gas pressure of the positive pressure pump 103. In some embodiments, when the first pressure regulating device 118 increases the pumping gas pressure by the positive pressure pump 103, the flow rate of the solution from the liquid chamber 102 to the bioreactor 50 is accelerated. In some embodiments, when the first pressure regulating device 118 reduces the pumping gas pressure by the positive pressure pump 103, the flow rate of the solution from the liquid chamber 102 to the bioreactor 50 is slowed down.

In some embodiments, the second pressure regulating device 119 is disposed at an outlet of the negative pressure pump 104 for regulating the suction gas pressure of the negative pressure pump 104. In some embodiments, when the second pressure regulating device 119 increases the suction gas pressure of the negative pressure pump 104, the flow rate of the solution from the bioreactor 50 to the liquid chamber 102 is accelerated. In some embodiments, when the second pressure regulating device 119 reduces the suction gas pressure of the negative pressure pump 104, the flow rate of the solution from the bioreactor 50 to the liquid chamber 102 is slowed down.

In some embodiments, solenoid valves 123 are respectively provided on a negative pressure branch 1053 and a positive pressure branch 1052. When the positive pressure pump 103 is running, the solenoid valve 123 on the positive pressure branch 1052 is opened, and the solenoid valve 123 on the negative pressure branch 1053 is closed; when the negative pressure pump 104 is running, the solenoid valve 123 on the negative pressure branch 1053 is closed, and the solenoid valve 123 on the positive pressure branch 1052 is closed. By setting the solenoid valve 123, the positive pressure branch 1052 and the negative pressure branch 1053 may be cut off and connected in time according to the pumping state of the positive pressure pump 103 and the negative pressure pump 104, and the rise or drop of the solution in the liquid chamber 102 may be controlled more accurately.

In some embodiments, the biological filtration system 10 further includes a pressure relief bypass 120, which is disposed on the flow path between the liquid chamber 102 and the positive pressure pump 103 and/or the negative pressure pump 104, to release the gas pressure in the biological filtration system 10.

In some embodiments, after the first sensor 111 or the second sensor 112 detects the liquid level information, the positive pressure pump 103 or the negative pressure pump 104 stops running. Since positive pressure or negative pressure still exists in the liquid chamber 102, the solution may continue to flow along the original flow direction. To make the solution in the liquid chamber 102 stop quickly at the high liquid level line and the low liquid level line, after the positive pressure pump 103 or the negative pressure pump 104 stops running, the pressure relief bypass 120 may be opened to connect the liquid chamber 102 to the outside, which may balance the pressure of the gas in the liquid chamber 102 with the outside air, so that the solution may be quickly stopped at the high liquid level line or the low liquid level line. In some embodiments, after the pressure relief bypass 120 is opened, the positive pressure and negative pressure inside the liquid chamber 102 may reach equilibrium with the atmospheric pressure in a very short time (e.g., 1 second, 2 seconds, 5 seconds, etc.), so that the liquid level line of the solution stops quickly.

In some embodiments, the pressure relief bypass 120 may include a bypass conduit and a pressure relief valve, one end of the pressure relief valve is communicated with the outside, and the other end is communicated with the liquid chamber 102 through the bypass conduit. When the pressure relief valve is opened, the positive pressure of the gas in the liquid chamber 102 may be released from the pressure relief valve, or the external gas may quickly supplement the negative pressure of the gas in the liquid chamber 102 to balance the gas with the external pressure. When the pressure relief valve is closed, the pressure within the liquid chamber 102 is regulated by the pressure regulating device.

In some embodiments, the filter device 101 is provided with a penetrating port 1015, and the biological filtration system 10 further includes a collection container 121, the penetrating port 1015 is connected to the collection container 121, and the collection container 121 is used to collect and hold the penetrating liquid.

In some embodiments, the biological filtration system 10 also includes a flow controlling device 122, and the flow controlling device 122 is disposed between the collection container 121 and the filter device 101, for controlling the flow rate of the solution in the filter device 101 to the collection container 121. The flow rate may be the discharge rate of the penetrating liquid in the filter device 101, and by adjusting the flow rate, that is, the discharge rate of the penetrating liquid, the filter penetrating rate of the filter device 101 is adjusted. By setting the flow controlling device 122, it is possible to control an appropriate penetrating rate according to different components of the solution and/or different filtration requirements, thereby improving the filtration effect.

In some embodiments, the flow controlling device 122 may be a peristaltic pump, and the flow rate of the solution in the filter device 101 to the collection container 121 is regulated by adjusting the power of the peristaltic pump.

In some embodiments, the biological filtration system 10 further includes at least one pressure sensor 124 for detecting the pressure signal of the solution and/or gas. In some embodiments, the pressure signal of the biological filtration system 10 detected by the pressure sensor 124 may be compared with a preset pressure threshold, and based on the comparison result, determining whether there is a blockage in the biological filtration system 10, and providing alarm information to the user.

In embodiment 1, referring to FIGS. 1A and 1B, the pressure sensor 124 is disposed on the flow path between the liquid chamber 102 and the positive pressure pump 103 and/or the negative pressure pump 104 to detect the pressure of the positive pressure branch 1052 and the negative pressure branch 1053, that is, the positive pressure branch 1052 and the negative pressure branch 1053 may be respectively provided with pressure sensors 124. In some embodiments, on the positive pressure branch 1052, the pressure sensor 124 may be provided between the solenoid valve 123 and the first pressure regulating device 118, and on the negative pressure branch 1053, the pressure sensor 124 may be provided between the solenoid valve 123 and the second pressure regulating device 119. In some embodiments, when the solenoid valve 123 of the positive pressure branch 1052 or the negative pressure branch 1053 is opened, the first pressure regulating device 118 and the second pressure regulating device 119 may perform more accurate operations of pressure regulation according to the pressure value fed back by the pressure sensor 124. In some embodiments, if the pressure sensor 124 detects that the pressure is too high, it may be determined that there is a blockage between the liquid chamber 102 and the positive pressure pump 103 or the negative pressure pump 104.

In some embodiments, the pressure sensor 124 may be disposed between the filter device 101 and collection container 121. For example, the pressure sensor 124 may be disposed between the flow controlling device 122 and the filter device 101. In some embodiments, if the pressure sensor 124 detects that the pressure is too high, it means that there is a blockage between the flow controlling device 122 and the filter device 101; if the pressure sensor 124 detects that the pressure is too low, it means that there is a blockage in the filter element of the filter device 101.

In some embodiments, the pressure sensor 124 may also be disposed between the filter device 101 and the bioreactor 50. For example, the pressure sensor 124 is disposed on the first conduit 106 as shown in FIG. 1A, or the pressure sensor 124 is disposed on the second conduit 107 and the third conduit 108 as shown in FIG. 1B. If the pressure sensor 124 detects that the pressure is too high, it means that there is a blockage in the conduit corresponding to the pressure sensor 124.

Figure 2A:
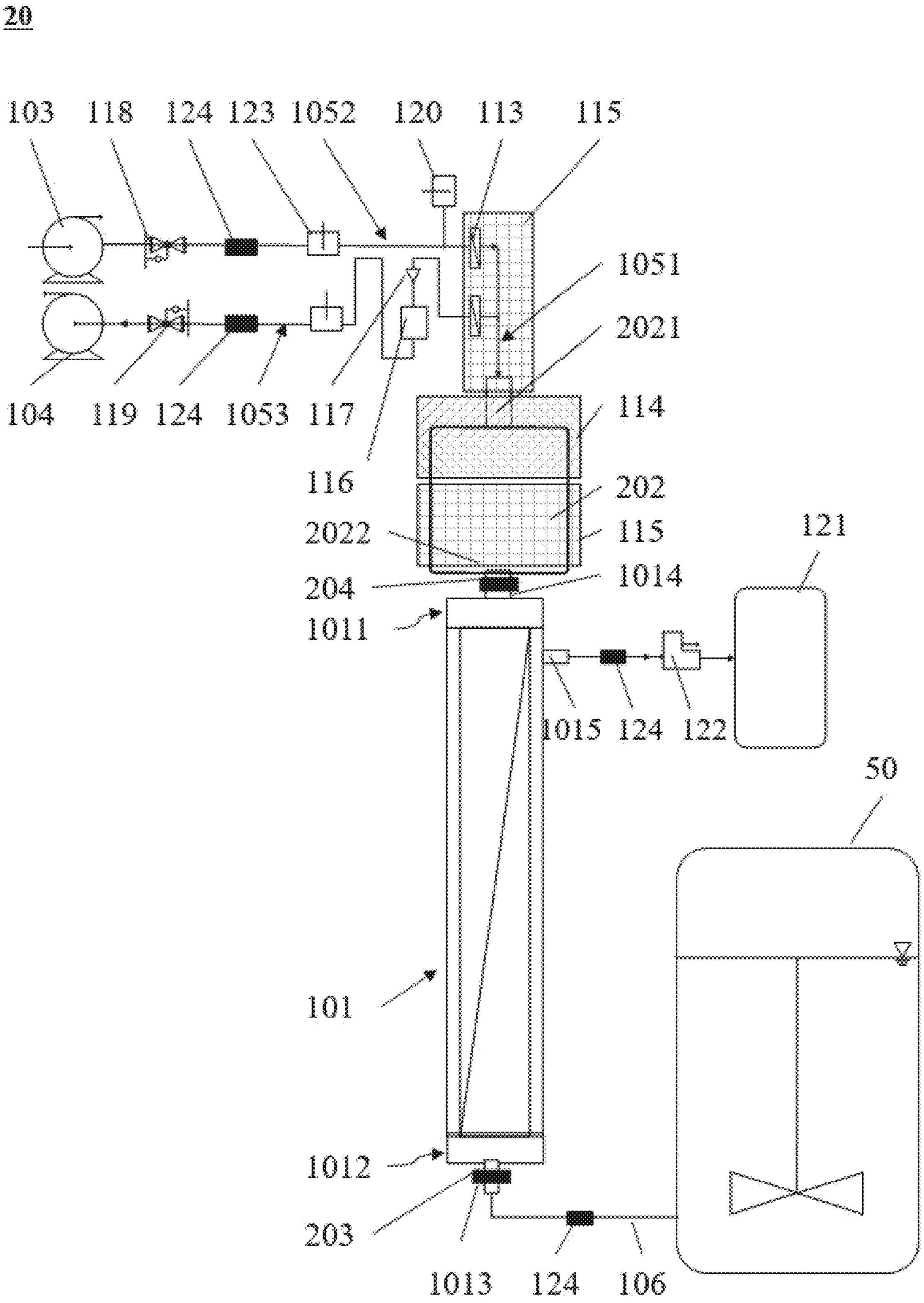
FIG. 2A is a schematic diagram illustrating an exemplary biological filtration system according to embodiment 2 of the present disclosure.
Figure 2B:
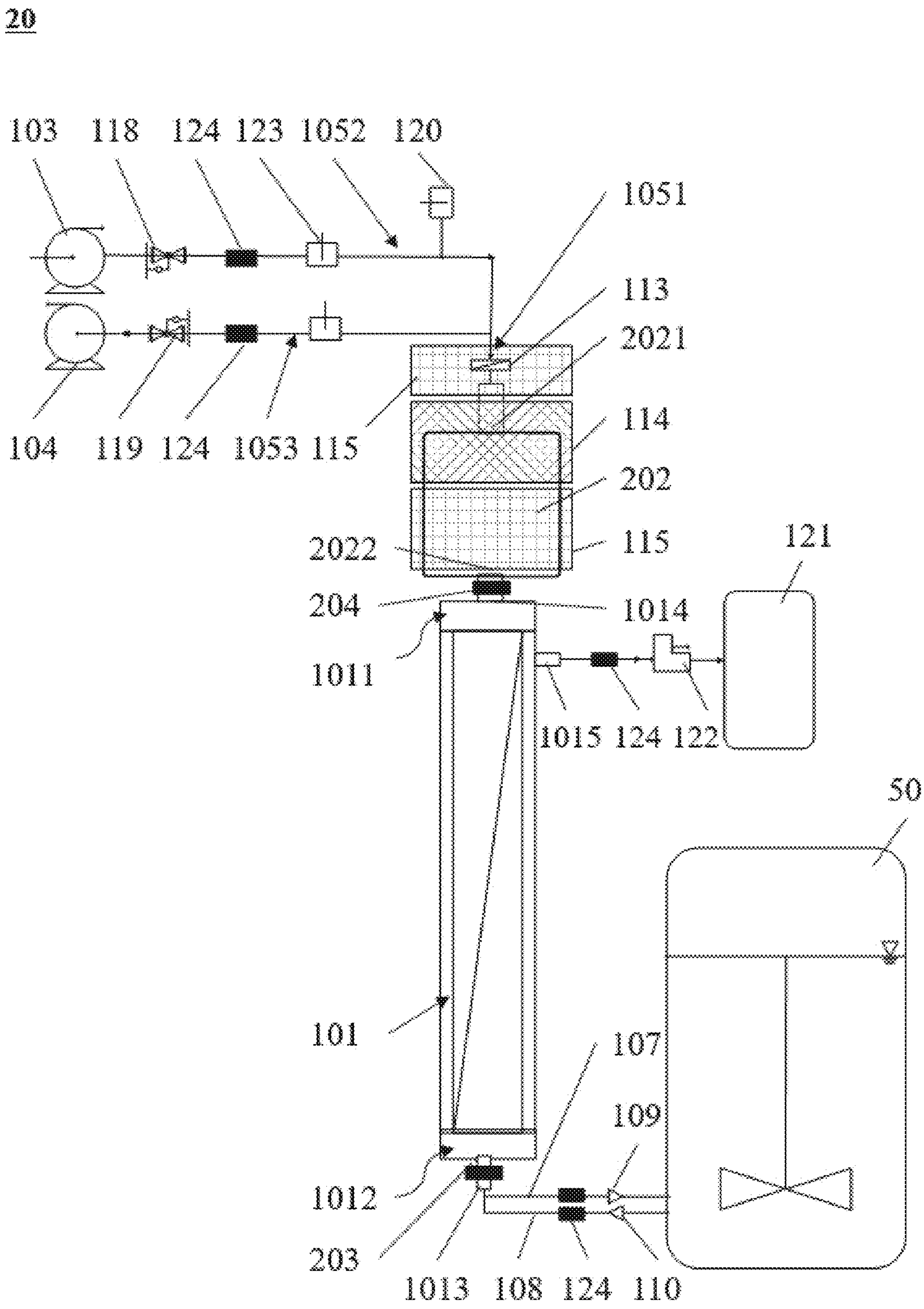
FIG. 2B is a schematic diagram illustrating an exemplary biological filtration system according to embodiment 2 of the present disclosure.

FIG. 2A and FIG. 2B are schematic diagrams illustrating an exemplary biological filtration system according to embodiment 2 of the present disclosure.

Referring to FIG. 2A and FIG. 2B, embodiment 2 of the present disclosure also provides a biological filtration system 20. It should be noted that most of the structures in embodiment 2 may refer to the biological filtration system 10 and its related descriptions shown in FIG. 1A and FIG. 1B. The following may mainly describe the different parts of embodiment 2 relative to embodiment 1, and the same structure will not be repeated.

The liquid chamber 202 in embodiment 2 of the present disclosure is disposed outside the filter device 101. In some embodiments, the liquid chamber 202 includes a single chamber that interfaces directly with the top end 1011 of the filter device 101. Interfacing directly means that the two components are directly connected without other structures, for example, the interface of the liquid chamber 202 and the retentate liquid port 1014 of the filter device 101 are directly connected.

In some embodiments, the liquid chamber 202 includes a first interface 2021 and a second interface 2022. The first interface 2021 is disposed at the top end of the chamber, and the second interface 2022 is disposed at the bottom end of the chamber. In some embodiments, the first interface 2021 is in fluid communication with the positive pressure pump 103 and the negative pressure pump 104, for example, through a three-way conduit. For details, referring to FIG. 1A and FIG. 1B and related descriptions. In some embodiments, the second interface 2022 is directly connected to the filter device 101, that is, the second interface 2022 may be directly connected to the retentate liquid port 1014 of the filter device 101. The liquid chamber 202 is directly connected to the filter device 101, which may reduce the amount of conduit, thereby reducing the fluid resistance of the solution.

In some embodiments, the liquid chamber 202 may be a container for storing solutions, and the first sensor 111 and the second sensor 112 may be provided inside the liquid chamber 202 to detect the liquid level information in the liquid chamber 202. For details, referring to FIG. 1A and FIG. 1B and associated description.

In some embodiments, the liquid chamber 202 may be a chamber that provides a buffer space for the solution flowing out of the filter device 101, that is, after the solution reaches the top of the filter device 101, the solution enters the liquid chamber 202 under the action of inertia, the liquid chamber 202 provides a buffer space for the solution, which may prevent the solution from flowing into components such as the gas purifier 113. In some embodiments, the solution is mainly circulated between the filter device 101 and the bioreactor 50, and no liquid is stored in the liquid chamber 202 for a long time, so the circulation amount of the solution outside the bioreactor 50 and the filter device 101 may be effectively reduced.

Referring to FIG. 2A and FIG. 2B, in some embodiments, the liquid chamber 202 acts as a buffer space for the solution, the solution mainly circulates between the filter device 101 and the bioreactor 50, and the negative pressure pump 104 makes the solution flow from the bioreactor 50 into the filter device 101 until the filter device 101 is full, and the positive pressure pump 103 makes the solution flow from the filter device 101 into the bioreactor 50 until the filter device 101 is emptied. The biological filtration system 20 further includes a third sensor 203 and a fourth sensor 204 for detecting liquid level information in the filter device 101, the third sensor 203 is disposed at the reaction liquid port 1013 of the filter device 101, and the fourth sensor 204 is disposed at the retentate liquid port 1014 of the filter device 101. In some embodiments, the third sensor 203 and the fourth sensor 204 include, but are not limited to, various types of sensors such as a contact liquid level sensor and a non-contact liquid level sensor.

In some embodiments, the third sensor 203 may detect whether the solution enters the filter device smoothly when the biological filtration system starts to work, and the fourth sensor 204 may detect whether the solution fills the filter device when the biological filtration system starts to work.

In some embodiments, when the positive pressure pump 103 operates, the gas applies positive pressure to the solution in the filter device 101 through the liquid chamber 202, and the solution in the filter device 101 flows to the bioreactor 50. When the liquid level in the filter device 101 drops to the position of the third sensor 203, the third sensor 203 is triggered to respond, and the operation of the positive pressure pump 103 is stopped at this time.

In some embodiments, when the negative pressure pump 104 operates, the gas in the filter device 101 is drawn out to provide negative pressure, and the solution in the bioreactor 50 flows to the filter device 101. When the liquid level in the filter device rises to the position of the fourth sensor 204, the fourth sensor 204 is triggered to respond, and the operation of the negative pressure pump 104 is stopped at this time, and the liquid chamber 202 provides a buffer for the solution reaching the position of the fourth sensor 204.

In some embodiments, the biological filtration system 20 may also be provided with a gas purifier 113 for purifying the gas entering and exiting the liquid chamber 202. In some embodiments, as shown in FIG. 2A, there may be two gas purifiers 113, which are respectively disposed on the positive pressure branch 1052 and the negative pressure branch 1053. By setting two gas purifiers 113, the gas in the positive pressure branch and the negative pressure branch may be filtered more accurately, and different types of gas purifiers may be installed according to the requirements of the filtration effect. In some embodiments, as shown in FIG. 2B, there may be one gas purifier 113, which is disposed on the circuit 1051 connected to the liquid chamber 202. By setting one gas purifier 113, the cost may be saved and the number of components of the biological filtration system may be simplified.

In some embodiments, to reduce the moisture content of the gas entering the gas purifier 113, the cooling device 114 may be disposed around the liquid chamber 202 to condense the moisture of the gas in the liquid chamber 202 into condensed water. In some embodiments, the cooling device 114 may be disposed at the upper half of the liquid chamber 202 to avoid affecting the temperature of the solution buffered to the lower half of the liquid chamber 202. For other descriptions of the gas purifier 113 and the cooling device 114, referring to FIG. 1A and FIG. 1B and related descriptions.

In some embodiments, referring to FIG. 2A, the liquid storage box 116 and the check valve 117 may be disposed on the negative pressure branch 1053 for collecting the condensed water and preventing the condensed water from flowing back into the gas purifier 113. For other descriptions of the liquid storage box 116 and the check valve 117, referring to FIG. 1A and FIG. 1B and related descriptions. In some embodiments, referring to FIG. 2B, the liquid storage box 116 and the check valve 117 may also be eliminated on the negative pressure branch 1053 to simplify the overall structure.

In some embodiments, to maintain the temperature of the solution in the filter device 101 and prevent the solution from entering the liquid chamber 202 for cooling and affecting the filtration effect, the outer surface of the liquid chamber 202 may further be provided with the heating device 115, and the heating device 115 corresponds to the lower half of the chamber 202 may provide heat for the solution buffered to the lower half of the liquid chamber 202. For other descriptions of the heating device 115, referring to FIG. 1A and FIG. 1B and related descriptions.

In some embodiments, referring to FIG. 2A, the filter device 101 and the bioreactor 50 may be connected through the first conduit 106. In some embodiments, referring to FIG. 2B, the filter device 101 and the bioreactor 50 may be connected by the second conduit 107 and the third conduit 108. For the connection between the filter device 101 and the bioreactor 50, referring to FIG. 1A and FIG. 1B and their related descriptions.

FIG. 3A to FIG. 3D are schematic diagrams illustrating an exemplary biological filtration system according to embodiment 3 of the present disclosure.

Referring to FIG. 3A to FIG. 3D, embodiment 3 of the present disclosure also provides a biological filtration system 30. First of all, it should be noted that most of the structures in embodiment 3 may refer to the biological filtration system and its related description shown in FIG. 1A to FIG. 2B. In the following, different parts of embodiment 3 relative to embodiment 1 and embodiment 2 may be mainly described, and the same structure will not be repeated.

The liquid chamber 302 in embodiment 3 of the present disclosure is provided separately from the filter device 101 and is in fluid communication through a conduit, which may increase the flexibility of the arrangement position of the liquid chamber 302. In some embodiments, the liquid chamber 302 includes a single chamber that is connected to the top end 1011 or the bottom end 1012 of the filter device 101 through the conduit. In some embodiments, referring to FIG. 3A, FIG. 3B, and FIG. 3D, the liquid chamber 302 is connected to the retentate liquid port 1014 of the top end 1011 of the filter device 101 through the conduit. In some embodiments, referring to FIG. 3C, the liquid chamber 302 is connected to the reaction liquid port 1013 of the bottom end 1012 of the filter device 101 through the conduit.

Figure 3A:
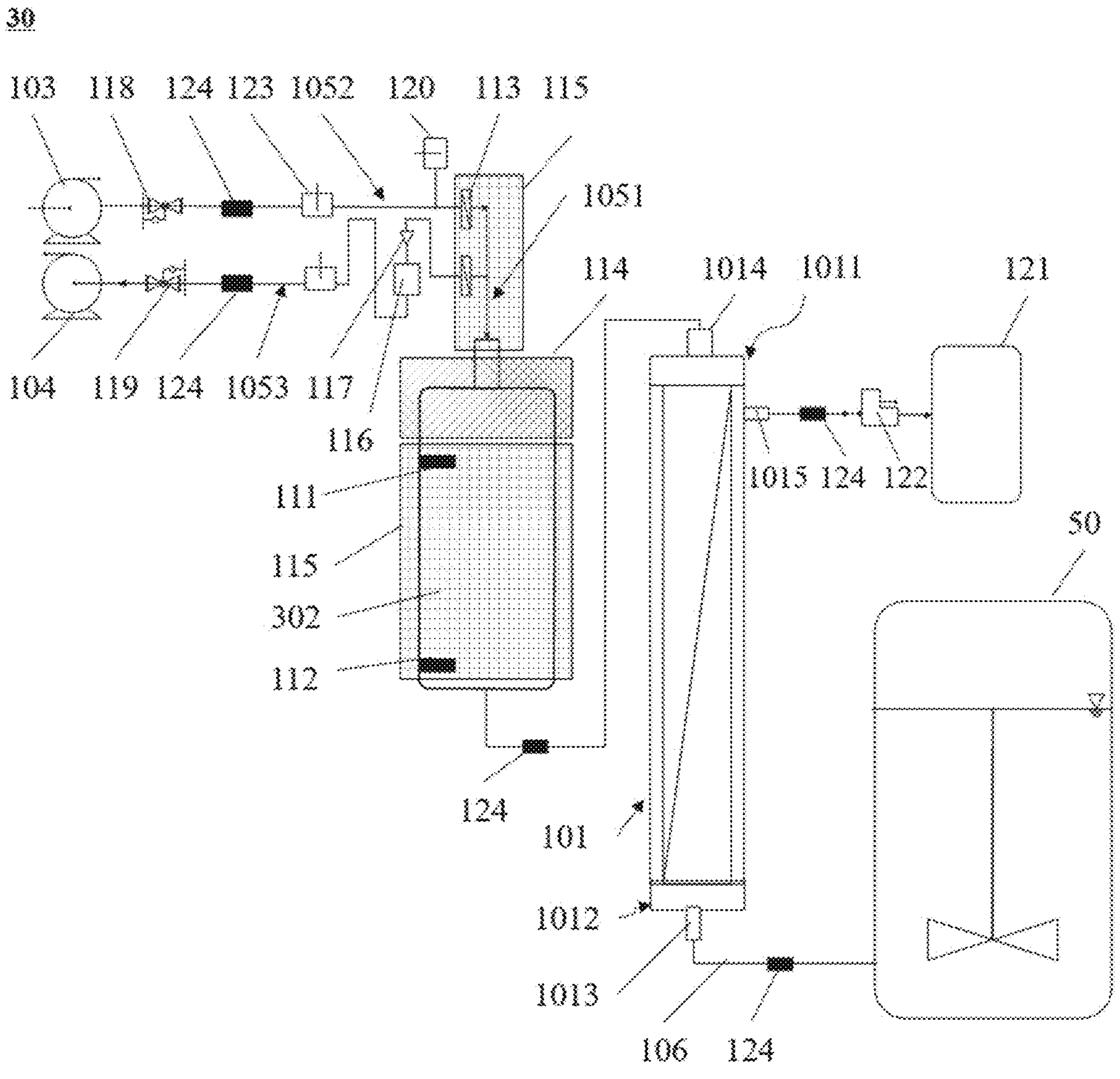
FIG. 3A is a schematic diagram illustrating an exemplary biological filtration system according to embodiment 3 of the present disclosure.
Figure 3B:
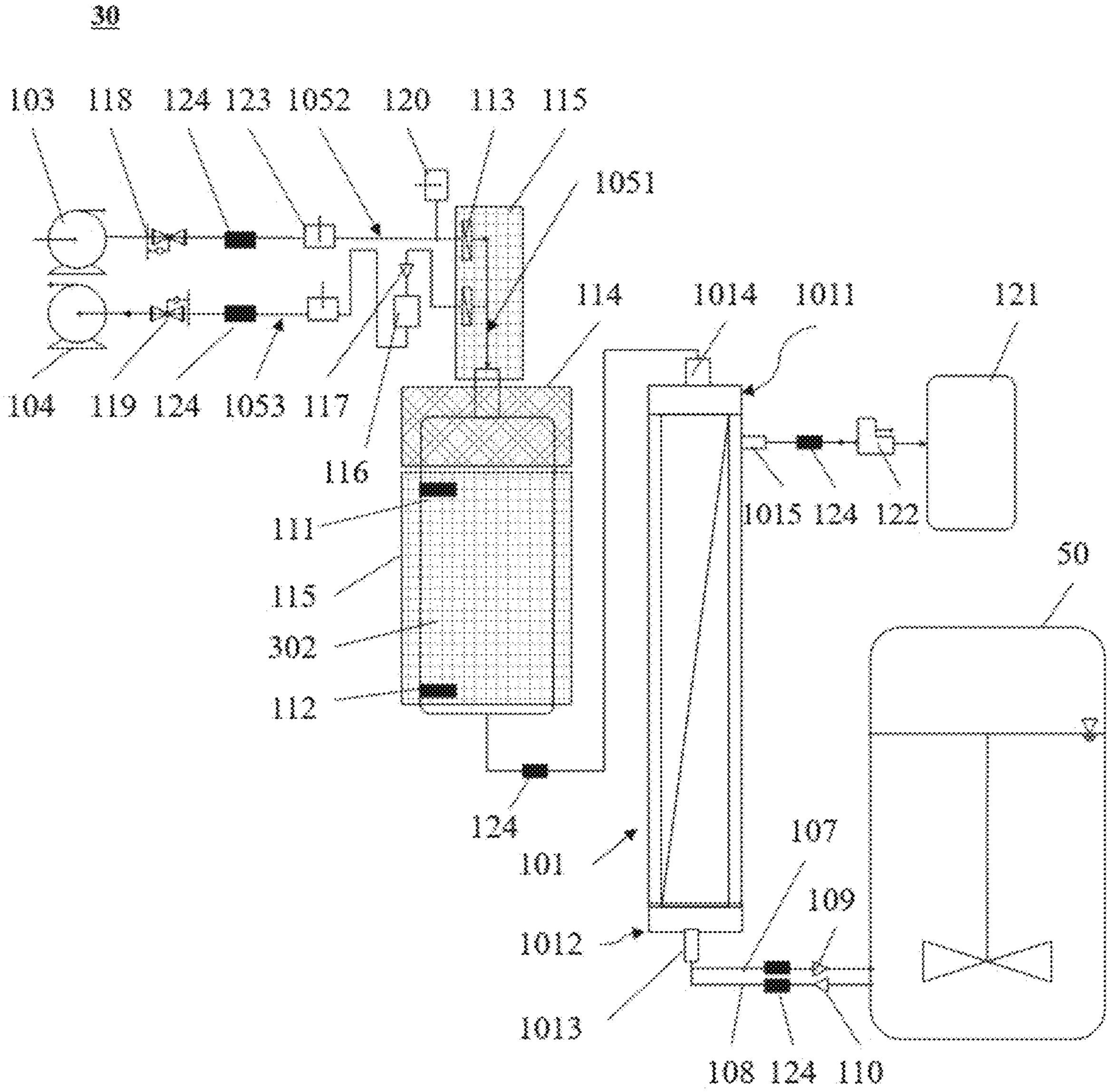
FIG. 3B is a schematic diagram illustrating an exemplary biological filtration system according to embodiment 3 of the present disclosure.

In some embodiments, one of the top end 1011 and the bottom end 1012 of the filter device 101 is used in fluid communication with the bioreactor 50 to filter the solution in the bioreactor 50. Referring to FIG. 3A, FIG. 3B and FIG. 3D, the bioreactor 50 is connected to the reaction liquid port 1013 of the bottom end 1012 of the filter device 101 through the conduit. In some embodiments, referring to FIG. 3C, the bioreactor 50 is connected to the retentate liquid port 1014 of the top end 1011 of the filter device 101 through the conduit. In some embodiments, referring to FIG. 3C and FIG. 3D, the liquid chamber 302 and the bioreactor 50 are also connected through the conduit.

In embodiment 3, referring to FIG. 3A, the reaction liquid port 1013 of the bottom end 1012 of the filter device 101 may be connected to the bioreactor 50 through the first conduit 106. The positive pressure pump 103 and the negative pressure pump 104 are used to drive the solution to flow back and forth between the filter device 101 and the bioreactor 50 through the first conduit 106. For more features of the first conduit 106, referring to FIG. 1A and its related description.

Referring to FIG. 3B, the reaction liquid port 1013 of the bottom end 1012 of the filter device 101 may be connected to the bioreactor 50 through the second conduit 107 and the third conduit 108. The positive pressure pump 103 is used to drive the solution to flow from the filter device 101 to the bioreactor 50 through the second conduit 107, and the negative pressure pump 104 is used to drive the solution to flow from the bioreactor 50 to the filter device 101 through the third conduit 108. For more features of the second conduit 107 and the third conduit 108, referring to FIG. 1B and its related description.

In some embodiments, the biological filtration system 30 includes a fourth conduit 125, a fifth conduit 126 and a sixth conduit 127, and one of the top end 1011 and the bottom end 1012 of the filter device 101 is connected to the chamber through the fourth conduit 125, the other one of the top end 1011 and the bottom end 1012 of the filter device 101 is connected to the bioreactor 50 through the fifth conduit 126, and the chamber is connected to the bioreactor 50 through the sixth conduit 127. The filter device 101, the bioreactor 50 and the liquid chamber 302 are connected by the fourth conduit 125, the fifth conduit 126 and the sixth conduit 127 to form a circuit, and the positive pressure pump 103 and the negative pressure pump 104 drive the solution to flow circularly in the circuit, this connection method enables the solution to flow in one direction in the filter device 101 to achieve continuous filtration and improve filtration efficiency.

Figure 3C:
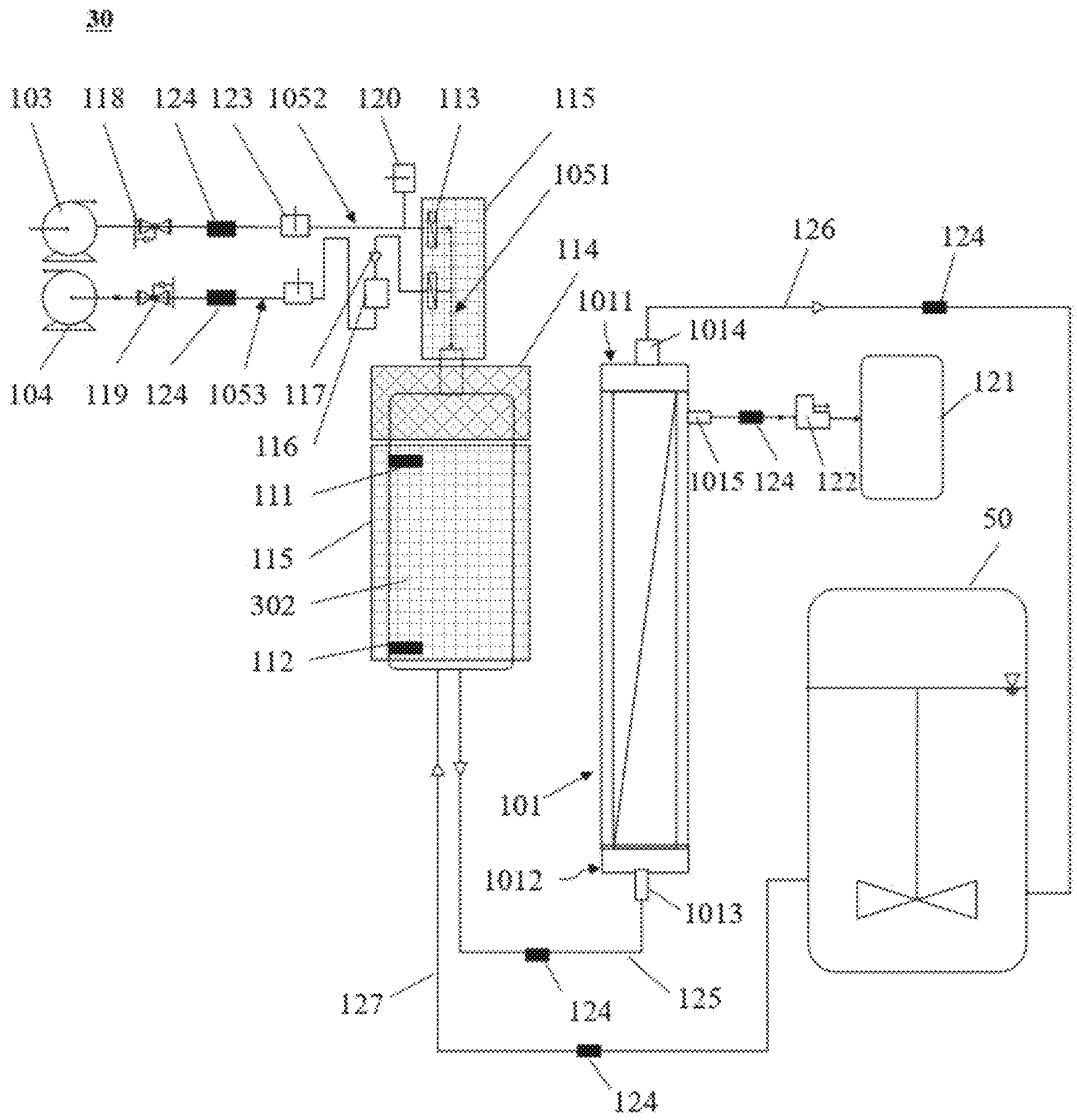
FIG. 3C is a schematic diagram illustrating an exemplary biological filtration system according to embodiment 3 of the present disclosure.
Figure 3D:
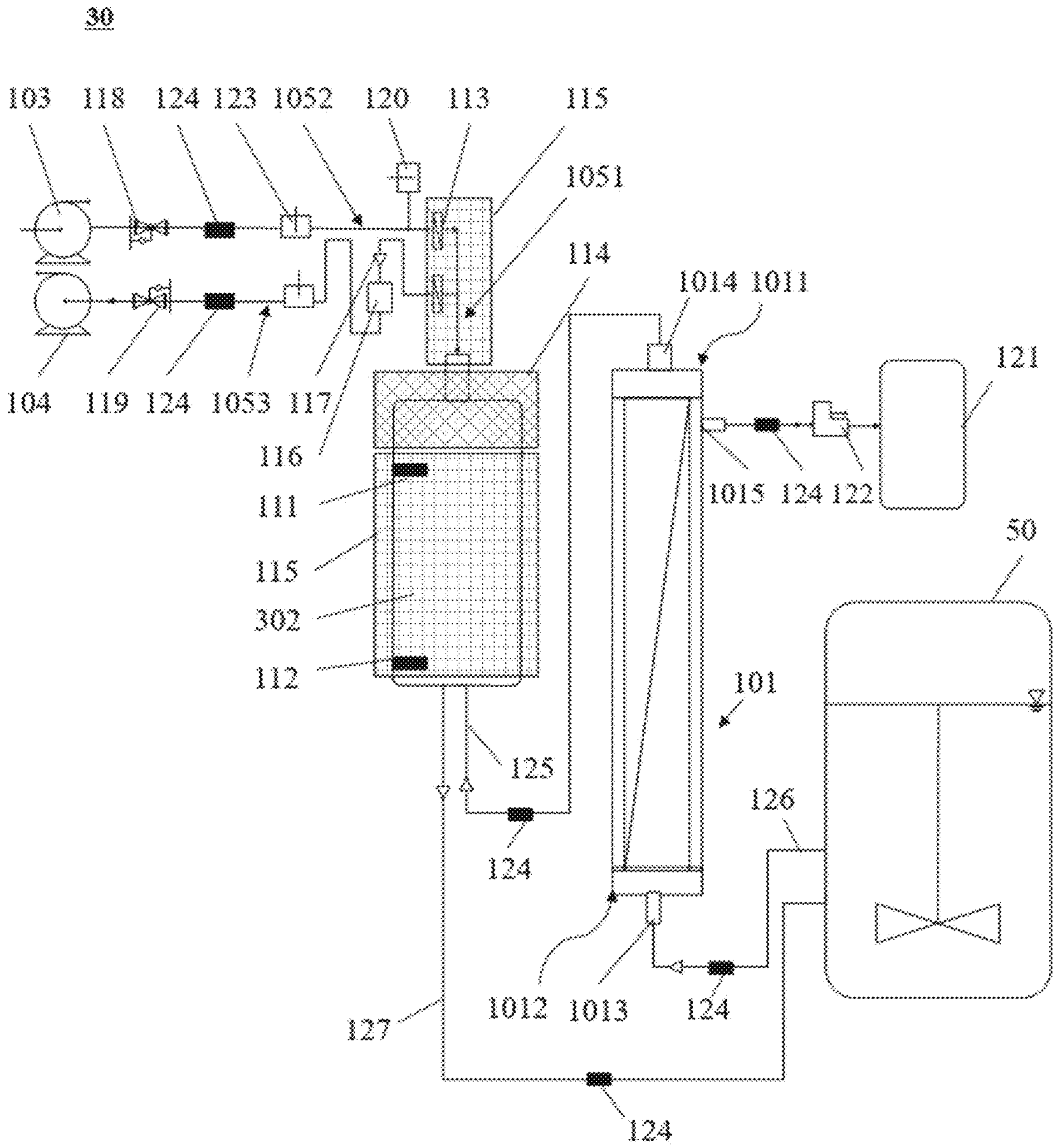
FIG. 3D is a schematic diagram illustrating an exemplary biological filtration system according to embodiment 3 of the present disclosure.

In some embodiments, referring to FIG. 3C, the bottom end 1012 of the filter device 101 is connected to the liquid chamber 302 through the fourth conduit 125, that is, the reaction liquid port 1013 of the filter device 101 is connected to the liquid chamber 302; the top end 1011 of the filter device 101 is connected to the bioreactor 50 through the fifth conduit 126, that is, the retentate liquid port 1014 of the filter device 101 is connected to the bioreactor 50; the liquid chamber 302 is connected to the bioreactor 50 through the sixth conduit 127.

In some embodiments, the positive pressure pump 103 is used to drive the solution in the chamber to flow to the bioreactor 50 through the filter device 101, and the negative pressure pump 104 is used to drive the solution in the bioreactor 50 to flow to the chamber, so that the solution flows circularly along the filter device 101, the bioreactor 50 and the liquid chamber 302 in sequence.

In some embodiments, the fourth conduit 125, the fifth conduit 126 and the sixth conduit 127 are respectively provided with a one-way valve, the one-way valve of the fourth conduit 125 is used to make the solution in the liquid chamber 302 flow to the filter device 101 in one direction, the one-way valve of the fifth conduit 126 is used to make the solution in the filter device 101 flow to the bioreactor 50 in one direction, and the one-way valve of the sixth conduit 127 is used to make the solution in the bioreactor 50 flow to the liquid chamber 302 in one direction. Backflow of the solution in the flow direction may be avoided by setting the one-way valve.

In some embodiments, referring to FIG. 3D, the top end 1011 of the filter device 101 is connected to the liquid chamber 302 through the fourth conduit 125, that is, the retentate liquid port 1014 of the filter device 101 is connected to the liquid chamber 302; the bottom end 1012 of the filter device 101 is connected to the bioreactor 50 through the fifth conduit 126, that is, the reaction liquid port 1013 of the filter device 101 is connected to the bioreactor 50; the liquid chamber 302 is connected to the bioreactor 50 through the sixth conduit 127.

In some embodiments, the positive pressure pump 103 is used to drive the solution in the chamber to flow to the bioreactor 50, and the negative pressure pump 104 is used to drive the solution in the bioreactor 50 to flow to the chamber through the filter device 101 to form a circuit, so that the solution flows circularly in the liquid chamber 302, the bioreactor 50 and the filter device 101 in sequence.

In some embodiments, the fourth conduit 125, the fifth conduit 126 and the sixth conduit 127 are respectively provided with the one-way valve, the one-way valve of the fourth conduit 125 is used to make the solution in the filter device 101 flow to the liquid chamber 302 in one direction, the one-way valve of the fifth conduit 126 is used to make the solution in the bioreactor 50 flow to the filter device 101 in one direction, the one-way valve of the sixth conduit 127 is used to make the solution in the liquid chamber 302 flow to the bioreactor 50 in one direction.

Referring to FIG. 3C and FIG. 3D, different connection modes of the fourth conduit 125, the fifth conduit 126 and the sixth conduit 127 make the solution have opposite flow directions in the filter device 101, the bioreactor 50 and the liquid chamber 302, and biological filtration system with different flow directions may be selected according to the properties of the solution. For example, for the solution in FIG. 3C, the solution flows out of the bioreactor 50 and enters the liquid chamber 302 first, so that the solution may be buffered and left for a period of time in the liquid chamber 302, which may reduce the entry of air bubbles into the filter device 101. For another example, for the solution in FIG. 3D, the solution flows directly into the filter device 101 from the bioreactor 50 for filtration, and the solution flowing out from the filter device 101 may be buffered in the liquid chamber 302 and left for a period of time before entering the bioreactor 50, which reduces the entry of air bubbles into the bioreactor 50.

In some embodiments, the liquid chamber 302 is further provided with the first sensor 111 and the second sensor 112, the first sensor 111 is used to detect whether the solution in the liquid chamber 302 reaches the high liquid level line, and the second sensor 112 is used to detect whether the solution in the liquid chamber 302 reaches the low liquid level line.

In some embodiments, the biological filtration system 30 also includes at least one pressure sensor 124. In some embodiments, referring to FIGS. 3A-3D, the pressure sensor 124 may be disposed on the flow path between the filter device 101 and the liquid chamber 302 to detect if there is a blockage therebetween. In some embodiments, the pressure sensor 124 may be disposed on the flow path between the filter device 101 and the bioreactor 50 to detect if there is a blockage therebetween. In some embodiments, referring to FIG. 3C and FIG. 3D, the pressure sensor 124 may be disposed on the flow path between the bioreactor 50 and the liquid chamber 302 to detect if there is a blockage therebetween. For other features and other arrangements of the pressure sensor 124, referring to FIG. 1A and FIG. 1B and their associated descriptions.

In some embodiments, the above-mentioned flow paths may all be provided with pressure sensors 124. In some embodiments, some of the above-mentioned flow paths are provided with pressure sensors 124, and the rest of the flow paths are not provided with pressure sensors 124. The embodiments of the present disclosure do not limit this.

Figure 4A:
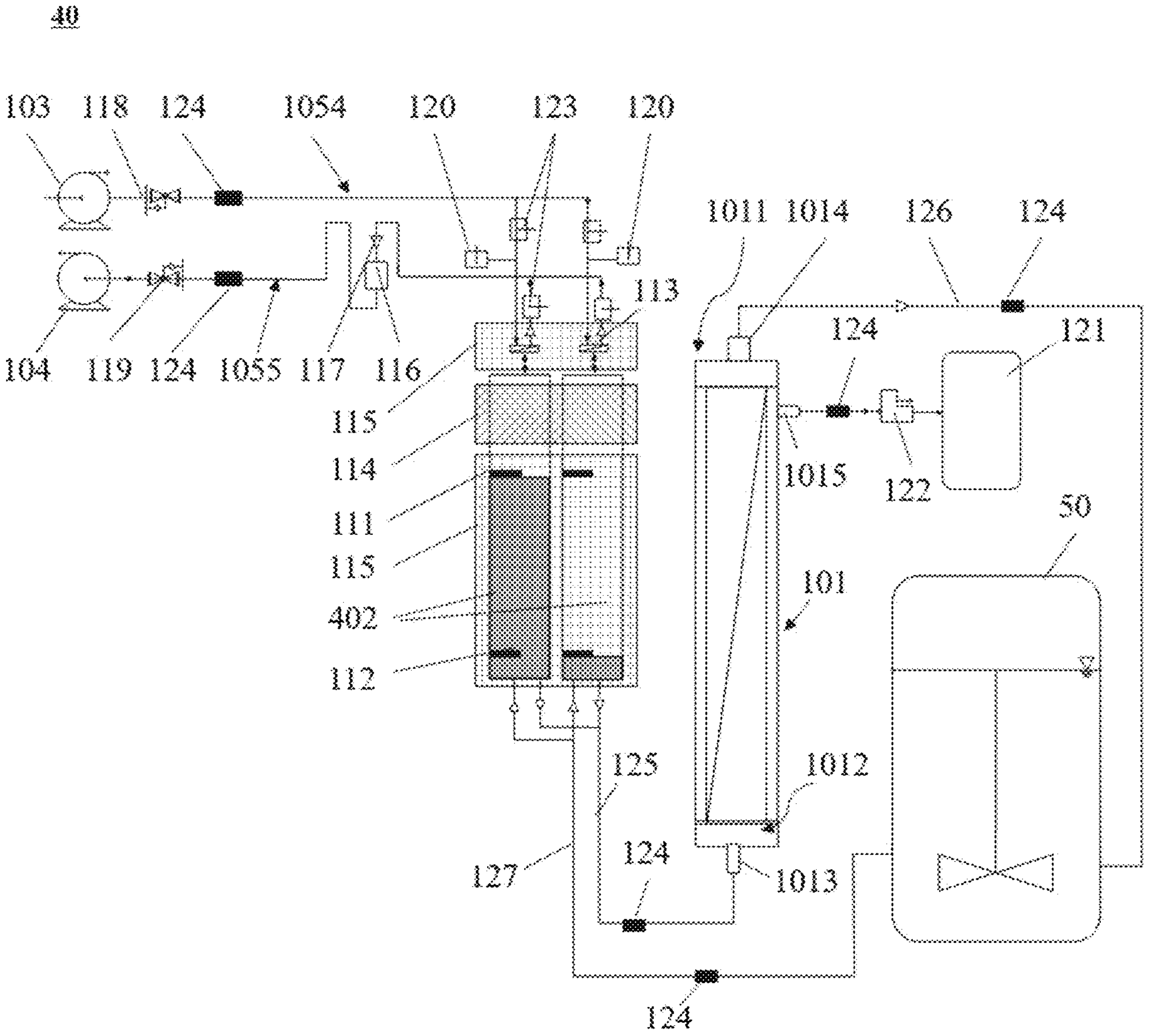
FIG. 4A is a schematic diagram illustrating an exemplary biological filtration system according to embodiment 4 of the present disclosure.
Figure 4B:
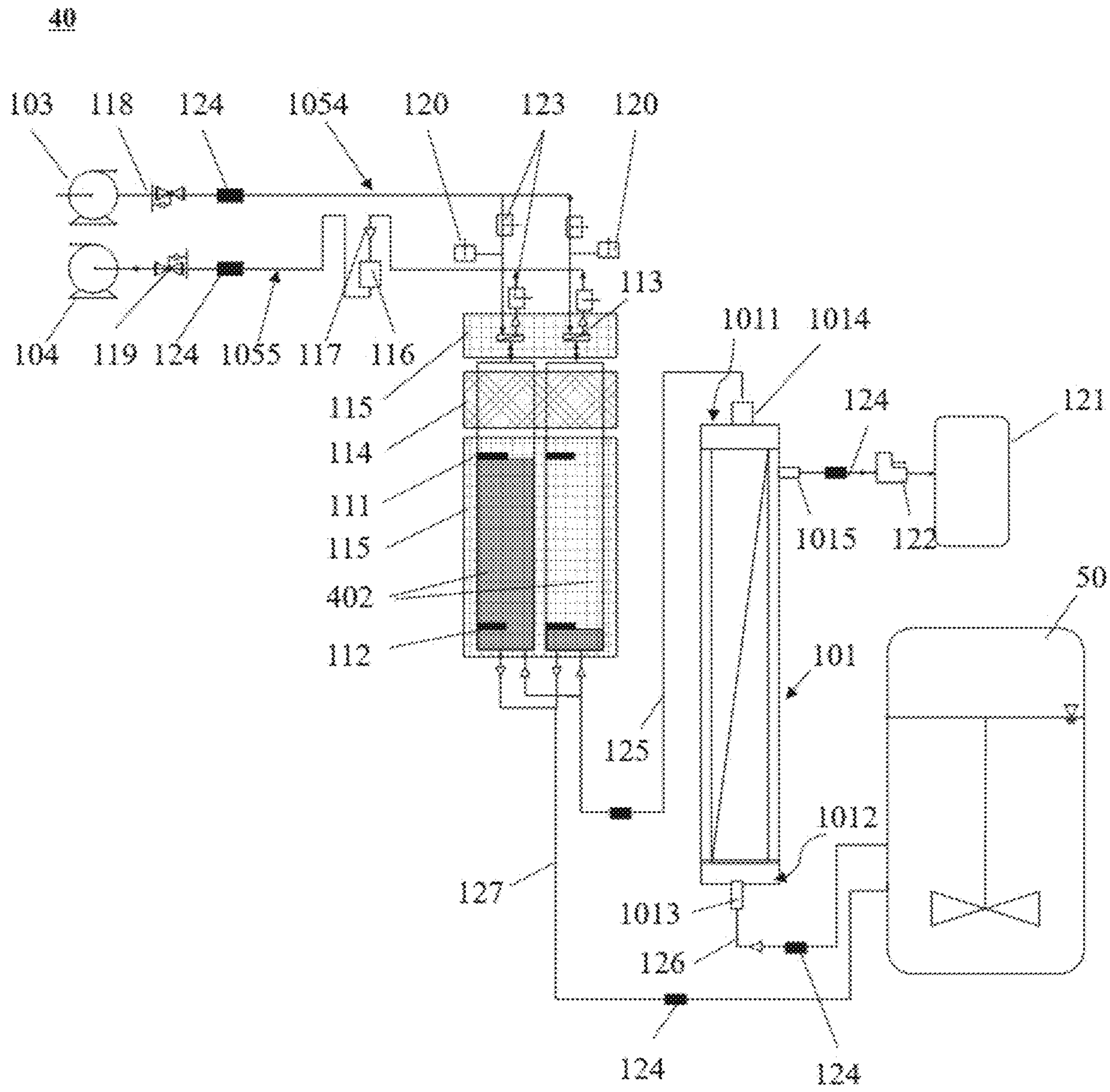
FIG. 4B is a schematic diagram illustrating an exemplary biological filtration system according to embodiment 4 of the present disclosure.
Figure 4C:
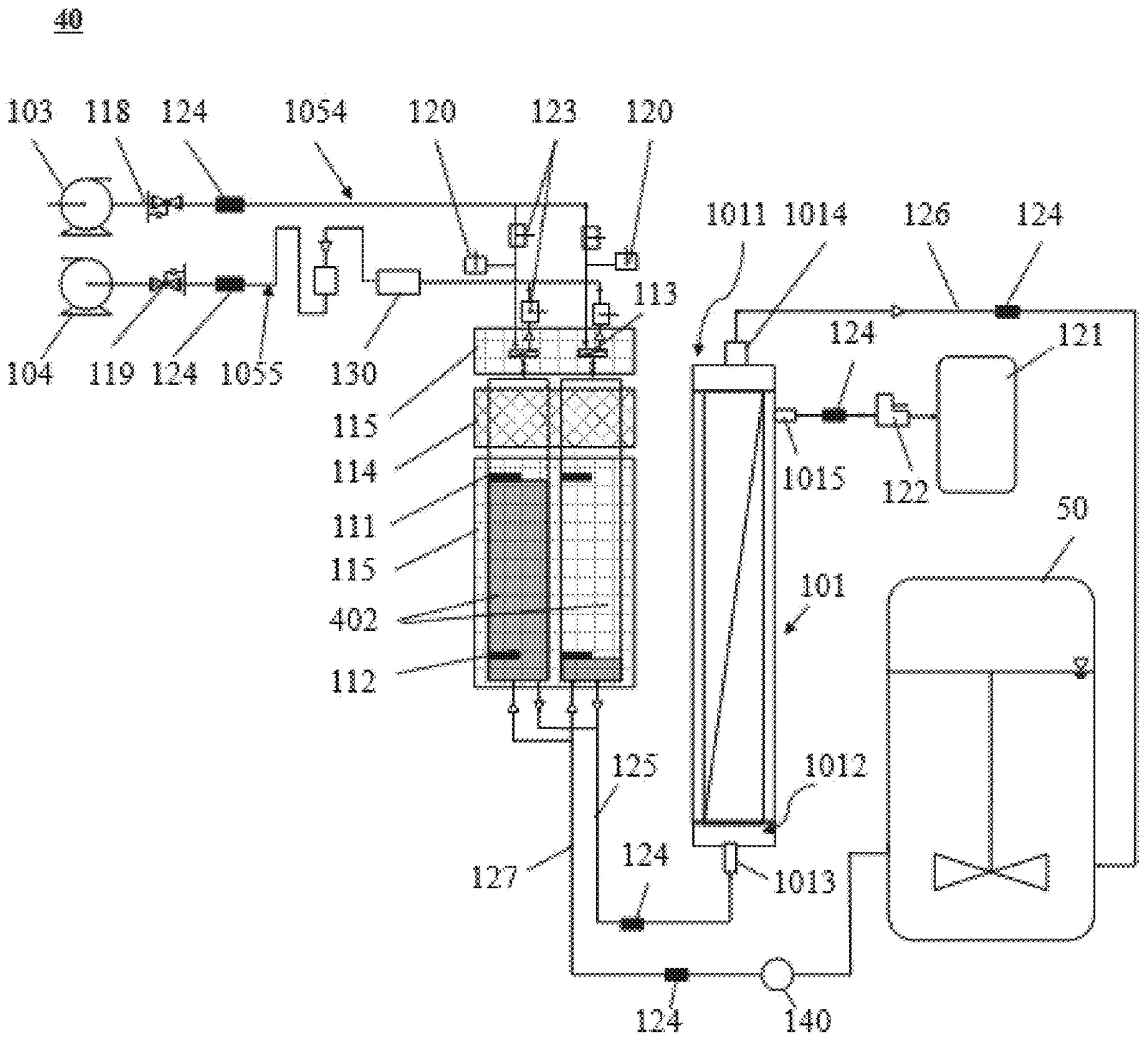
FIG. 4C is a schematic diagram illustrating an exemplary biological filtration system according to embodiment 4 of the present disclosure.

FIG. 4A and FIG. 4C are schematic diagrams illustrating an exemplary biological filtration system according to embodiment 4 of the present disclosure.

Referring to FIG. 4A to FIG. 4C, embodiment 4 of the present disclosure also provides a biological filtration system 40. First of all, it should be noted that most of the structures in embodiment 4 may refer to the biological filtration system and the related description shown in FIGS. 1A to 3D. In the following, different parts of embodiment 4 relative to embodiment 1 will be mainly described, and the same structure will not be repeated.

The liquid chamber 402 in embodiment 4 of the present disclosure is provided separately from the filter device 101 and includes a plurality of chambers, each chamber is in fluid communication with the positive pressure pump 103 or the negative pressure pump 104 respectively, and each chamber is respectively connected with the filter device 101. In some embodiments, while the positive pressure pump 103 delivers positive pressure to part of the chambers, the negative pressure pump 104 delivers negative pressure to another part of the chambers, to improve the filtration efficiency of the solution between the filter device 101 and the bioreactor 50. In some embodiments, the number of chambers may be 2-10, for example, may be 2, 3, 4, 6, etc., which is not limited in the present disclosure.

In some embodiments, the positive pressure pump 103 may be in fluid communication with the plurality of chambers through the first multiway conduit 1054. In some embodiments, the first multiway conduit 1054 includes a first main circuit and a plurality of first branches, one end of the first main circuit is connected to the positive pressure pump 103, and the plurality of first branches are respectively connected to the multiple chambers one by one. In some embodiments, each first branch is provided with a solenoid valve 123 respectively, and the solenoid valve 123 is used to control the on and off of each first branch respectively.

In some embodiments, the negative pressure pump 104 may be in fluid communication with the plurality of chambers through the second multiway conduit 1055. In some embodiments, the second multiway conduit 1055 includes a second main circuit and a plurality of second branches, one end of the second main circuit is connected to the positive pressure pump 103, and the plurality of second branches are respectively connected to the multiple cavities one by one. In some embodiments, each second branch is provided with a solenoid valve 123 respectively, and the solenoid valve 123 is used to control the on and off of each second branch respectively.

In some embodiments, each chamber is connected to the top end 1011 or the bottom end 1012 of the filter device 101 through a conduit, for example, multiple chambers may be connected to the filter device 101 through a multiway conduit. In some embodiments, the biological filtration system 40 includes a fourth conduit 125, a fifth conduit 126 and a sixth conduit 127, the fourth conduit 125 is connected between the liquid chamber 402 and the filter device 101, the fifth conduit 126 is connected between the bioreactor 50 and the filter device 101, and the sixth conduit 127 is connected between the bioreactor 50 and the liquid chamber 402. The fourth conduit 125 and the sixth conduit 127 may be multiway conduits that may communicate with each chamber respectively.

In some embodiments, referring to FIG. 4A, the liquid chamber 402 is connected to the reaction liquid port 1013 at the bottom end 1012 of the filter device 101 through the fourth conduit 125, and the retentate liquid port 1014 at the top end of the filter device 101 is connected to the bioreactor 50 through the fifth conduit 126, and the bioreactor 50 is connected to the liquid chamber 402 through the sixth conduit 127.

In some embodiments, one-way valves are also disposed on the fourth conduit 125, the fifth conduit 126, and the sixth conduit 127, respectively. The one-way valve of the fourth conduit 125 is used to make the solution in the liquid chamber 402 flow to the filter device 101 in one direction, and the one-way valve of the fifth conduit 126 is used to make the solution in the filter device 101 flow to the bioreactor 50 in one direction, the one-way valve of the sixth conduit 127 is used to make the solution in the bioreactor 50 flow to the liquid chamber 402 in one direction.

In some embodiments, the liquid chamber 402 having two chambers is used as an example to illustrate the circulation process of the solution between the biological filtration system 40 and the bioreactor 50. The liquid chamber 402 includes a first chamber and a second chamber. When the biological filtration system 40 is working, the negative pressure pump 104 provides negative pressure to the first chamber to drive the solution in the bioreactor 50 to flow to the first chamber, the positive pressure pump 103 and the negative pressure pump 104 work at the same time, the positive pressure pump 103 provides positive pressure to the second chamber, drives the solution in the second cavity to flow to the filter device 101, and flows to the bioreactor 50 after being filtered by the filter device 101. When the solution in the first chamber reaches the first sensor 111 and the solution in the second chamber reaches the second sensor 112, the negative pressure pump 104 provides negative pressure to the second chamber, drives the solution in the bioreactor 50 to flow to the second chamber, the positive pressure pump 103 provides positive pressure to the first chamber, and drives the solution in the first chamber to flow to the filter device 101, and then flow to the bioreactor 50 after being filtered by the filter device 101. The solution in the biological filtration system 40 flows circularly continuously according to such a law.

In some embodiments, referring to FIG. 4B, the liquid chamber 402 is connected to the retentate liquid port 1014 of the top end 1011 of the filter device 101 through the fourth conduit 125, and the reaction liquid port 1013 of the bottom end 1012 of the filter device 101 is connected to the filter device 101 through the fifth conduit 126, and the bioreactor 50 is connected to the liquid chamber 402 through the sixth conduit 127.

In some embodiments, the fourth conduit 125, the fifth conduit 126 and the sixth conduit 127 are also respectively provided with a one-way valve. The one-way valve of the fourth conduit 125 is used to make the solution in the filter device 101 flow to the liquid chamber 402 in one direction, the one-way valve of the fifth conduit 126 is used to make the solution in the bioreactor 50 flow to the filter device 101 in one direction, and the one-way valve of the sixth conduit 127 is used to make the solution in the liquid chamber 402 flow to bioreactor 50 in one direction. The solution circulation process in this scheme is similar to that in the scheme in FIG. 4A, the only difference is that the flow direction of the solution is different from that in the scheme in FIG. 4A, which will not be repeated in the present disclosure.

In some embodiments, referring to FIG. 4C, the biological filtration system 40 further includes a negative pressure buffer chamber 130, and the negative pressure buffer chamber 130 is disposed on a flow path between the negative pressure pump 104 and the liquid chamber 402. For example, the negative pressure buffer chamber 130 is disposed on the second main circuit of the second multiway conduit 1055. The negative pressure buffer chamber 130 is configured as a hollow chamber, one side of the negative pressure buffer chamber 130 is connected to the negative pressure pump 104 through a conduit, and the other side is connected to the liquid chamber 402 through a conduit.

In some embodiments, the negative pressure buffer chamber 130 is configured to control a rising height of the solution in the liquid chamber 402. According to FIG. 4A and related descriptions, during the circulation of the solution between the biological filtration system 40 and the bioreactor 50, when the liquid chamber 402 needs negative pressure to make the solution in the bioreactor 50 enter the liquid chamber 402, the negative pressure buffer chamber 130 may be used to control the rising height of the solution entering the liquid chamber 402. For example, first, the flow path between the negative pressure buffer chamber 130 and the liquid chamber 402 is in a non-conductive state, the flow path between the negative pressure buffer chamber 130 and the negative pressure pump 104 is in a conductive state, the negative pressure pump 104 provides negative pressure to the negative pressure buffer chamber 130, and at this time, the negative pressure buffer chamber 130 may form a negative pressure. Next, after the negative pressure formed in the negative pressure buffer chamber 130 reaches a preset pressure value, the flow path between the negative pressure buffer chamber 130 and the negative pressure pump 104 is switched to a non-conductive state. Then, when the negative pressure buffer chamber 130 works, the flow path between the negative pressure buffer chamber 130 and the liquid chamber 402 is switched to a conductive state, and the negative pressure in the negative pressure buffer chamber 130 attracts the liquid chamber 402, so that the solution in the bioreactor 50 enters liquid chamber 402. During this process, the amount of the solution entering the liquid chamber 402 and the attainable height are related to the volume and negative pressure value in the negative pressure buffer chamber 130. By setting the pressure value in the negative pressure buffer chamber 130, the rising height of the solution in the liquid chamber 402 may be controlled.

In some embodiments, the negative pressure buffer chamber 130 may replace the first sensor 111 in the liquid chamber 402, that is, the first sensor 111 is not disposed on the liquid chamber 402, and the negative pressure buffer chamber 130 is configured to control the liquid chamber 402, so the first sensor 111 does not need to detect the liquid level height in the liquid chamber 402. By predetermining a maximum height of the solution allowed by the liquid chamber 402 to rise, and calculating the preset pressure value of the negative pressure buffer chamber 130 based on the maximum height, the negative pressure of the preset pressure value (or lower than the preset pressure value) is provided to the negative pressure buffer chamber 130 through the negative pressure pump 104 in advance, so as to ensure that the liquid level in the liquid chamber 402 reaches (or does not exceed) the maximum height. In some embodiments, the first sensor 111 is disposed in the liquid chamber 402, the negative pressure buffer chamber 130 may cooperate with the first sensor 111 in the liquid chamber 402, and the first sensor 111 detects whether the solution exceeds the maximum height in the liquid chamber 402, the negative pressure buffer chamber 130 controls the rising height of the solution in the liquid chamber 402.

During the use of the biological filtration system 40, an unstable positive pressure may exist in the bioreactor 50. When the negative pressure pump 104 is used to drive the solution in the bioreactor 50 to the liquid chamber 402, the positive pressure in the bioreactor 50 may disturb the pressure of the entire circulation loop, causing the solution to flow too fast and/or causing the liquid level in the liquid chamber 402 to exceed the maximum height, thereby having an impact on the safety and controllability of the biological filtration system 40. In some embodiments, as the negative pressure buffer chamber 130 is provided, and when the negative pressure buffer chamber 130 is working, the flow path between the negative pressure buffer chamber 130 and the negative pressure pump 104 is in a non-conducting state (i.e., a closed state), so that after the liquid level reaches the maximum height, it is difficult to change the liquid level in the liquid chamber 402 even if the positive pressure acts on the solution in the liquid chamber 402.

In some embodiments, a second pressure regulating device 119 is disposed between the negative pressure pump 104 and the negative pressure buffer chamber 130, and the second pressure regulating device 119 is used to control the suction gas pressure of the negative pressure pump 104 to the negative pressure buffer chamber 130. During the working process of the negative pressure pump 104, the second pressure regulating device 119 may adjust the negative pressure output by the negative pressure pump 104 to the pressure range required by the negative pressure buffer chamber 130. For example, the required pressure in the negative pressure buffer chamber 130 is 100 mPa, the negative pressure output by the negative pressure pump 104 is 200 mPa, the negative pressure pump 104 inputs the negative pressure of 200 mPa to the second pressure regulating device 119, and the second pressure regulating device 119 may input the negative pressure of 100 mPa into the negative pressure buffer chamber 130 through its self-regulating function. When the pressure in the negative pressure buffer chamber 130 reaches the preset pressure value, the second pressure regulating device 119 is switched to the closed state, so that the flow path between the negative pressure pump 104 and the negative pressure buffer chamber 130 is non-conductive, and the negative pressure pump 104 stops working, and the negative pressure buffer chamber 130 forms a negative pressure corresponding to the preset pressure value.

In some embodiments, the second pressure regulating device 119 is a proportion regulating valve. In other embodiments, the second pressure regulating device 119 may also be other regulating valves, such as an electric regulating valve, a pneumatic regulating valve, and the like. For more details about the second pressure regulating device 119, referring to the relevant description in embodiment 1.

In some embodiments, a load cell (not shown in the figure) is disposed in the negative pressure buffer chamber 130 or between the negative pressure buffer chamber 130 and the negative pressure pump 104, and the load cell is used to detect the pressure in the negative pressure buffer chamber 130. In some embodiments, the load cell may be a pressure sensor 124 disposed between the negative pressure buffer chamber 130 and the negative pressure pump 104. In some embodiments, the load cell may be a different element from the pressure sensor 124. In some embodiments, the load cell may be disposed in the negative pressure buffer chamber 130.

In some embodiments, a solenoid valve 123 is disposed between the negative pressure buffer chamber 130 and the liquid chamber 402, and the solenoid valve 123 is used to control the conduction and cutoff between the negative pressure buffer chamber 130 and the liquid chamber 402. In some embodiments, the solenoid valve 123 may be disposed on the second branch of the second multiway conduit 1055 to facilitate the control of the conduction and cutoff between the corresponding chamber and the negative pressure buffer chamber 130. For more information about the solenoid valve 123, referring to the related description in embodiment 1.

In some embodiments, the biological filtration system 40 also includes a processor, and the solenoid valve 123 and the load cell are signal-connected to the processor through a wired or wireless manner, respectively, and the processor is used to control the solenoid valve 123 to close according to the signal of the load cell.

In some embodiments, the processor of the biological filtration system 40 may control the rising height of the solution into the liquid chamber 402 when it cooperates with the negative pressure buffer chamber 130, the load cell and the solenoid valve 123. For example, first, determining the maximum height that the liquid chamber 402 allows the solution to rise, and calculating the first negative pressure value that the negative pressure buffer chamber 130 needs to provide to the liquid chamber 402 to reach the maximum height. Next, the negative pressure pump 104 provides negative pressure of the first negative pressure value into the negative pressure buffer chamber 130, and the processor controls the second pressure regulating device 119 between the negative pressure buffer chamber 130 and the negative pressure pump 104 to close. Then, the processor controls the solenoid valve 123 between the negative pressure buffer chamber 130 and the liquid chamber 402 to open, and the negative pressure in the negative pressure buffer chamber 130 attracts the liquid chamber 402, so that the solution in the bioreactor 50 enters the liquid chamber 402, the negative pressure value in the negative pressure buffer chamber 130 decreases as the liquid level of the liquid chamber 402 rises. When the load cell detects that the negative pressure value in the negative pressure buffer chamber 130 drops to a set value (e.g., when the negative pressure in the negative pressure buffer chamber 130 and the liquid level of the liquid chamber 402 reach a balance), the processor controls the solenoid valve 123 to close, to stop the solution in the liquid chamber 402 from rising, so that the rising height of the solution may be controlled at the above-mentioned maximum height at this time. In some embodiments, the negative pressure provided by the negative pressure pump 104 into the negative pressure buffer chamber 130 may be greater than the first negative pressure value. At this time, the corresponding setting value when solenoid valve 123 is closed may be adjusted correspondingly to accurately control the rising height of the solution.

During the process of opening the solenoid valve 123 between the negative pressure buffer chamber 130 and the liquid chamber 402, generally speaking, the larger the negative pressure value in the negative pressure buffer chamber 130, the faster the flow rate of the solution entering the liquid chamber 402, so when the negative pressure value in the negative pressure buffer chamber 130 decreases as the liquid level rises, the flow rate of the solution entering the liquid chamber 402 also changes from fast to slow, and the change in the flow rate easily leads to unstable solution circulation. Therefore, in some embodiments, a throttle valve (not shown in the figure) is further disposed between the negative pressure buffer chamber 130 and the liquid chamber 402, and the throttle valve is used to control the flow rate of the solution in the liquid chamber 402 to the negative pressure buffer chamber 130. In some embodiments, the throttle valve may control the solution to enter the liquid chamber 402 at a constant or substantially constant flow rate so as not to affect the stability of the solution circulation.

In some embodiments, the throttle valve is signal-connected to the processor, for example, the throttle valve is signal-connected to the processor through a wired or wireless manner. The processor may send a control command to the throttle valve to adjust the opening degree of the throttle valve, so as to adjust the flow rate of the solution in the liquid chamber 402 flowing to the negative pressure buffer chamber 130.

In some embodiments, the throttle valve may be disposed between the negative pressure buffer chamber 130 and the solenoid valve 123. For example, the throttle valve may be disposed on the second main circuit of the second multiway conduit 1055, so as to facilitate multiple chambers of the liquid chamber 402 to share one throttle valve.

In some embodiments, a flow sensor 140 is disposed between the bioreactor 50 and the liquid chamber 402, and the flow sensor 140 is used to collect a flow signal of the solution of the bioreactor 50 flowing to the liquid chamber 402, and according to the flow signal, the circulating flow of the solution in the loop formed by the bioreactor 50, the liquid chamber 402 and the filter device 101 may be determined.

In some embodiments, the biological filtration system 40 further includes a processor, the flow sensor 140 is signal-connected to the processor, for example, connected to the processor in a wired or wireless manner, and the flow sensor 140 is further configured to send the flow signal to the processor. In some embodiments, the processor may store a preset circulating flow range, and after receiving the flow signal from the flow sensor 140, the processor compares the flow signal with the preset circulating flow range, and if the flow signal is lower than the preset circulating flow range, it means that the circulating flow of the biological filtration system 40 is too low, if the flow signal is within the preset circulating flow range, it means that the circulating flow of the biological filtration system 40 meets the requirements, if the flow signal is higher than the preset circulating flow range, it means that the circulating flow of the biological filtration system 40 is too high.

In some embodiments, the processor may control the flow rate of the solution of the biological filtration system 40 based on the flow signal. In some embodiments, the processor may determine whether the circulating flow of the biological filtration system 40 meets the requirements after comparing the flow signal with the preset circulating flow range. If the requirements are not met, the processor may control the pumping frequency of the negative pressure pump 104 and the positive pressure pump 103 to adjust the flow rate of the solution in the biological filtration system 40, or by controlling the negative pressure value of the negative pressure buffer chamber 130 and the pressure value of the positive pressure pump 103 to adjust the flow rate of the solution of the biological filtration system 40, thereby adjusting the circulating flow of the biological filtration system 40.

In some embodiments, the liquid chamber 402 includes a plurality of chambers, each chamber is in fluid communication with the other of the top end 1011 and the bottom end 1012 through conduits, respectively. That is, the negative pressure buffer chamber 130 and/or the flow sensor 140 described above may be applied to the two types of biological filtration systems 40 related to FIGS. 4A and 4B. In some embodiments, the liquid chamber may include 2, 3, 4, or other chambers.

In some embodiments, the negative pressure buffer chamber 130 may be applied to the biological filtration systems of embodiments 1-3. The negative pressure buffer chamber 130 may be disposed between the negative pressure pump 104 and the liquid chamber. The negative pressure pump 104 firstly makes the negative pressure buffer chamber 130 form negative pressure, and after the negative pressure in the negative pressure buffer chamber 130 reaches a preset pressure value, the negative pressure buffer chamber 130 attracts the liquid chamber, so that the solution in the bioreactor 50 enters the liquid chamber. By setting the volume and/or the negative pressure value of the negative pressure buffer chamber 130, the height of the solution rising in the liquid chamber may be controlled, so as to prevent the solution from rising too high and overflowing from the top end of the liquid chamber. In addition, the negative pressure buffer chamber 130 may balance the positive pressure in the circulation loop of the biological filtration system, reduce the pressure disturbance in the circulation loop, and improve the safety and controllability of the biological filtration system.

In some embodiments, the flow sensor 140 may be applied to the biological filtration systems of embodiments 1-3. The flow sensor 140 is used to collect the flow signal of the solution flowing from the bioreactor 50 to the liquid chamber, and according to the flow signal, the flow rate of the solution in the circulation loop may be controlled, thereby accurately adjusting the circulation efficiency of the bioreactor system.

The biological filtration systems in the embodiments 1 to 4 above may further include a processor, and the processor is configured to be signal-connected to each component in the biological filtration system, and may acquire signals of each component or send control instructions to each component. Specifically including:

In some embodiments, the processor is in signal communication with the first sensor 111 to the fourth sensor 204, may obtain the liquid level signals of the first sensor 111 to the fourth sensor 204, and process the liquid level signals.

In some embodiments, the processor is connected to the solenoid valves 123 of the positive pressure branch and the negative pressure branch, and may control the on and off of the solenoid valves 123 based on the liquid level signals fed back by the first sensor 111 to the fourth sensor 204.

In some embodiments, the processor is in signal communication with the positive pressure pump 103 and the negative pressure pump 104, and may control the activation and stop of the positive pressure pump 103 and the negative pressure pump 104 based on the liquid level signals fed back by the first sensor 111 to the fourth sensor 204.

In some embodiments, the processor is in signal communication with the solenoid valve 123 of the pressure relief bypass 120, and may selectively release the positive pressure or the negative pressure in the liquid chamber 102 based on the switching state of the positive pressure pump 103 and the negative pressure pump 104.

In some embodiments, the processor is connected to the pressure sensors 124 of the positive pressure branch and the negative pressure branch for obtaining pressure signals detected by the pressure sensors 124.

In some embodiments, the processor is in signal communication with the first pressure regulating device 118 and the second pressure regulating device 119 for controlling the first pressure regulating device 118 and the second pressure regulating device 119 to adjust the pressure of the positive pressure branch and the negative pressure branch based on the pressure signals fed back by the pressure sensors 124 of the positive pressure branch and the negative pressure branch.

In some embodiments, the processor is in signal communication with the flow controlling device 122 for controlling the flow controlling device 122 to regulate the flow rate of the solution into the collection container 121.

In some embodiments, the processor is in signal communication with the pressure sensor 124 between the liquid chamber 102 and the filter device 101, the pressure sensor 124 between the filter device 101 and the bioreactor 50, and the filter device 101, and the pressure sensor 124 between the filter device 101 and the collection container 121, to obtain the pressure signal of the pressure sensor 124 to determine whether there is a blockage in the biological filtration system.

Figure 5:
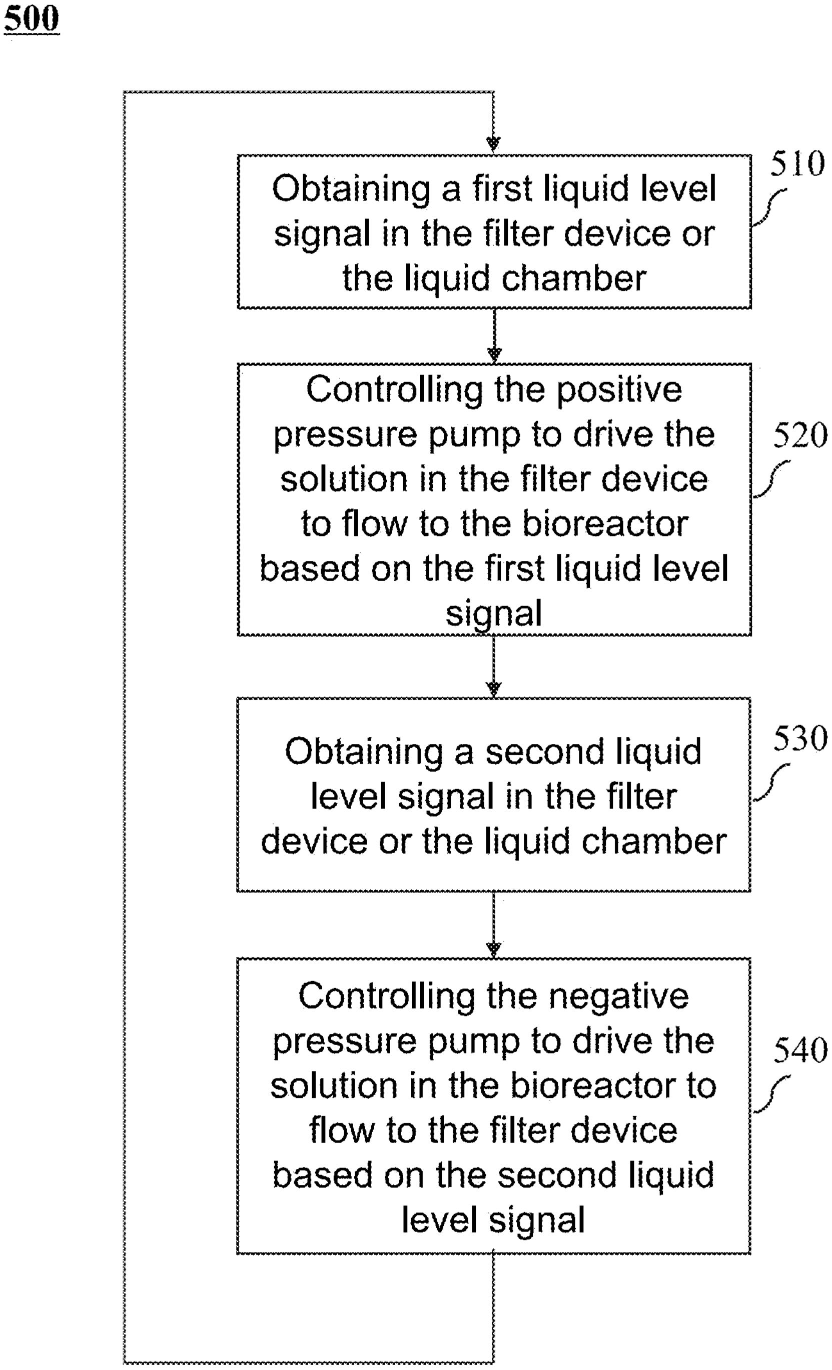
FIG. 5 is a flowchart illustrating a controlling method for an exemplary biological filtration system according to some embodiments of the present disclosure.

FIG. 5 is a flowchart illustrating a controlling method for an exemplary biological filtration system according to some embodiments of the present disclosure.

Referring to FIG. 5, in some embodiments, a controlling method for a biological filtration system may include a process 500. In some embodiments, the biological filtration system may further include a processor, and the process 500 may be performed by the processor and includes the following steps:

Step 510, obtaining a first liquid level signal in the filter device 101 or the liquid chamber 102.

In some embodiments, the first liquid level signal may be a signal triggered when the solution in the liquid chamber 102 or the filter device 101 is at a high liquid level line. In some embodiments, the first liquid level signal may be collected by the first sensor 111 or the fourth sensor 204. For more descriptions of the first sensor 111 and the fourth sensor 204, referring to FIGS. 1A to 4B and related descriptions.

In some embodiments, the first sensor 111 is disposed in the liquid chamber 102 and disposed at the top of the liquid chamber 102 at a preset interval. In some embodiments, when the solution in the liquid chamber 102 rises to the liquid level line corresponding to the first sensor 111, the first sensor 111 may be triggered to generate a first liquid level signal, and the first sensor 111 sends the first liquid level signal to the processor.

In some embodiments, the fourth sensor 204 is disposed at the retentate liquid port 1014 of the top end 1011 of the filter device 101. In some embodiments, when the solution in the filter device 101 rises to the retentate liquid port 1014 corresponding to the fourth sensor 204, the fourth sensor 204 may be triggered to generate a first liquid level signal, and the fourth sensor 204 sends the first liquid level signal to the processor.

Step 520, controlling the positive pressure pump 103 to drive the solution in the filter device 101 to flow to the bioreactor 50 based on the first liquid level signal.

In some embodiments, after the processor obtains the first liquid level signal, it may be determined that the liquid level of the solution in the filter device 101 or the liquid chamber 102 has risen to the high liquid level line marked by the first sensor 111 or the fourth sensor 204. Based on the first liquid level signal, the processor controls the positive pressure pump 103 to start, and the positive pressure pump 103 pumps gas to the liquid chamber 102 to provide positive pressure, thereby driving the solution in the filter device 101 to flow to the bioreactor 50, so that the liquid level of the solution in the filter device 101 or the liquid chamber 102 drops.

For the biological filtration system in the above-mentioned embodiment 1 to embodiment 4, controlling positive pressure pump 103 to drive the solution in the filter device 101 to flow to the bioreactor 50, including:

Step 1, closing the solenoid valve 123 between the negative pressure pump 104 and the chamber generating the first liquid level signal, and stopping supplying negative pressure to the chamber generating the first liquid level signal.

In some embodiments, the liquid chamber 102 includes a single chamber, and the corresponding chamber generating the first liquid level signal is the liquid chamber 102 itself, such as the biological filtration system in the embodiments 1-3. In some embodiments, the liquid chamber 102 includes a plurality of chambers, and the corresponding chamber generating the first liquid level signal is part of the chambers, such as the biological filtration system in embodiment 4.

In some embodiments, after obtaining the first liquid level signal, the processor closes the solenoid valve 123 between the negative pressure pump 104 and the chamber generating the first liquid level signal, and stops providing the negative pressure to the chamber generating the first liquid level signal, so that the solution will not continue to rise after reaching the high liquid level line.

For the biological filtration systems in embodiments 1 to 3, after obtaining the first liquid level signal, the processor may close the solenoid valve 123 on the negative pressure branch 1053, and the processor may also control the negative pressure pump 104 to stop running, to avoid the continued operation of the negative pressure pump 104 resulting in excessive negative pressure in the conduit between the solenoid valve 123 and the negative pressure pump 104.

For the biological filtration system in embodiment 4, after obtaining the first liquid level signal, the processor may close the solenoid valve 123 on the second multiway conduit 1055 to cut off the negative pressure pump 104 and the negative pressure of the chamber generating the first liquid level signal. However, at this time, the negative pressure pump 104 may continue to operate to provide negative pressure for other chambers that do not generate the first liquid level signal.

Step 2, opening the pressure relief bypass 120 to release the residual negative pressure in the chamber generating the first liquid level signal, and then closing the pressure relief bypass 120.

In some embodiments, after closing the solenoid valve 123, the processor controls the pressure relief bypass 120 to open, so that the external gas may quickly supplement the negative pressure of the gas in the liquid chamber 102, so that the solution and gas may reach an equilibrium state with the external pressure, to prevent the solution from continuing to rise or generate bubbles under the action of residual negative pressure.

In some embodiments, the time at which the pressure relief bypass 120 is opened may be determined by a timer. In some embodiments, the processor may preset the pressure relief time, and the preset pressure relief time refers to the time required after the pressure relief bypass 120 completes the relief of the residual negative pressure in the liquid chamber 102. In some embodiments, after the pressure relief bypass 120 is opened, the timer starts to count to obtain a timed pressure relief time, and when the timed pressure relief time is equal to the preset pressure relief time, the processor closes the pressure relief bypass 120.

In some embodiments, the pressure sensor 124 may determine the time at which pressure relief bypass 120 is open. In some embodiments, the pressure sensor 124 is provided on the pressure relief bypass 120 or on the conduit between the pressure relief bypass 120 and the liquid chamber. When the pressure value detected by the pressure sensor 124 is equal to the external atmospheric pressure, the processor closes the pressure relief bypass 120.

Step 3, opening the solenoid valve 123 between the positive pressure pump 103 and the chamber generating the first liquid level signal to provide the positive pressure to the chamber generating the first liquid level signal.

In some embodiments, after the residual negative pressure in the liquid chamber 102 is discharged, the solenoid valve 123 between the positive pressure pump 103 and the chamber generating the first liquid level signal is opened to provide the positive pressure to the chamber generating the first liquid level signal, which causes the liquid level of the solution to drop. For the biological filtration systems in the embodiments 1-3, the processor may open the solenoid valve 123 on the positive pressure branch 1052, and at the same time the processor controls the positive pressure pump 103 to start running, and the positive pressure pump 103 pumps gas to the liquid chamber 102 to provide the positive pressure. For the biological filtration system in embodiment 4, the processor may open the solenoid valve 123 on the first multiway conduit 1054, to conduct the positive pressure pump 103 and the chamber generating the first liquid level signal, and provide positive pressure to the chamber.

Step 530, obtaining a second liquid level signal in the filter device 101 or the liquid chamber 102.

In some embodiments, the second liquid level signal may be a signal triggered when the solution in the liquid chamber 102 or the filter device 101 is at a low liquid level line. In some embodiments, the second liquid level signal may be collected by the second sensor 112 or the third sensor 203. For more description of the second sensor 112 and the third sensor 203, referring to FIGS. 1A to 4B and related descriptions.

In some embodiments, the second sensor 112 is disposed at the bottom of the liquid chamber 102. In some embodiments, when the solution in the liquid chamber 102 drops to the liquid level line corresponding to the second sensor 112, the second sensor 112 may be triggered to generate a second liquid level signal, and the second sensor 112 may send the second liquid level signal to the processor.

In some embodiments, the third sensor 203 is disposed at the reaction liquid port 1013 of the bottom end 1012 of the filter device 101. In some embodiments, when the solution in the filter device 101 drops to the reaction liquid port 1013 corresponding to the third sensor 203, the third sensor 203 may be triggered to generate a second liquid level signal, and the third sensor 203 may send the second liquid level signal to the processor.

Step 540, controlling the negative pressure pump 104 to drive the solution in the bioreactor 50 to flow to the filter device 101 based on the second liquid level signal.

In some embodiments, after obtaining the second liquid level signal, the processor may determine that the liquid level of the solution in the filter device 101 or the liquid chamber 102 has dropped to the low liquid level line marked by the second sensor 112 or the third sensor 203. Based on the second liquid level signal, the processor controls the negative pressure pump 104 to start, and the negative pressure pump 104 pumps gas to the liquid chamber 102 to provide negative pressure, thereby driving the solution in the bioreactor 50 to flow to the filter device 101, so that the solution in the filter device 101 or the liquid chamber 102 rises.

For the biological filtration system in the above-mentioned embodiment 1 to embodiment 4, controlling the negative pressure pump 104 to drive the solution in the bioreactor 50 to flow to the filter device 101, including:

Step 1, closing the solenoid valve 123 between the positive pressure pump 103 and the chamber generating the second liquid level signal, and stopping supplying positive pressure to the chamber generating the second liquid level signal.

In some embodiments, the liquid chamber 102 includes a single chamber, and the corresponding chamber generating the second liquid level signal is the liquid chamber 102 itself, such as the biological filtration system in embodiments 1-3. In some embodiments, the liquid chamber 102 includes a plurality of chambers, and the chambers generating the second liquid level signal is part of the chambers, such as the biological filtration system in embodiment 4.

In some embodiments, after obtaining the second liquid level signal, the processor closes the solenoid valve 123 between the positive pressure pump 103 and the chamber generating the second liquid level signal, and stops providing the positive pressure to the chamber generating the second liquid level signal, so that the solution does not continue to drop after reaching the low liquid level line.

For the biological filtration systems in embodiments 1 to 3, after obtaining the second liquid level signal, the processor may close the solenoid valve 123 on the positive pressure branch 1052, and the processor may also control the positive pressure pump 103 to stop running to avoid the continued operation of the positive pressure pump 103 resulting in excessive positive pressure in the conduit between the solenoid valve 123 and the positive pressure pump 103.

For the biological filtration system in embodiment 4, after obtaining the second liquid level signal, the processor may close the solenoid valve 123 on the first multiway conduit 1054 to cut off the positive pressure pump 103 and the chamber generating the second liquid level signal. However, at this time, the positive pressure pump 103 may continue to operate to provide positive pressure for other chambers that do not generate the second liquid level signal.

Step 2, opening the pressure relief bypass 120 to release the residual positive pressure in the chamber generating the second liquid level signal, and then closing the pressure relief bypass 120.

In some embodiments, after closing the solenoid valve 123, the processor controls the pressure relief bypass 120 to open, so that the residual positive pressure in the liquid chamber 102 is released to the outside, so that the solution and gas may reach an equilibrium state with the external pressure, to prevent the solution from continuing to rise or generate bubbles under the action of residual positive pressure.

In some embodiments, the timer or the pressure sensor 124 may determine when the pressure relief bypass 120 is open. For more description of the timer or pressure sensor 124, referring to step 520 and its description.

Step 3, opening the solenoid valve 123 between the negative pressure pump 104 and the chamber generating the second liquid level signal, and providing negative pressure to the chamber generating the second liquid level signal.

In some embodiments, after the residual positive pressure in the liquid chamber 102 is discharged, the solenoid valve 123 between the negative pressure pump 104 and the chamber generating the second liquid level signal is opened to provide the negative pressure to the chamber generating the second liquid level signal, so that the liquid level of the solution rises. For the biological filtration systems in embodiments 1 to 3, the processor may open the solenoid valve 123 on the negative pressure branch 1053, and at the same time, the processor controls the negative pressure pump 104 to start running, and the negative pressure pump 104 sucks gas to provide the negative pressure to the liquid chamber 102. For the biological filtration system in embodiment 4, the processor may open the solenoid valve 123 on the second multiway conduit 1055 to conduct the negative pressure pump 104 and the chamber generating the second liquid level signal, and provide negative pressure to the chamber.

In some embodiments, after step 540 is performed, step 510 is returned to continue performing, and the cycle is repeated, so that the solution flows circularly and flows back and forth between the filter device 101 and the bioreactor 50.

Figure 6:
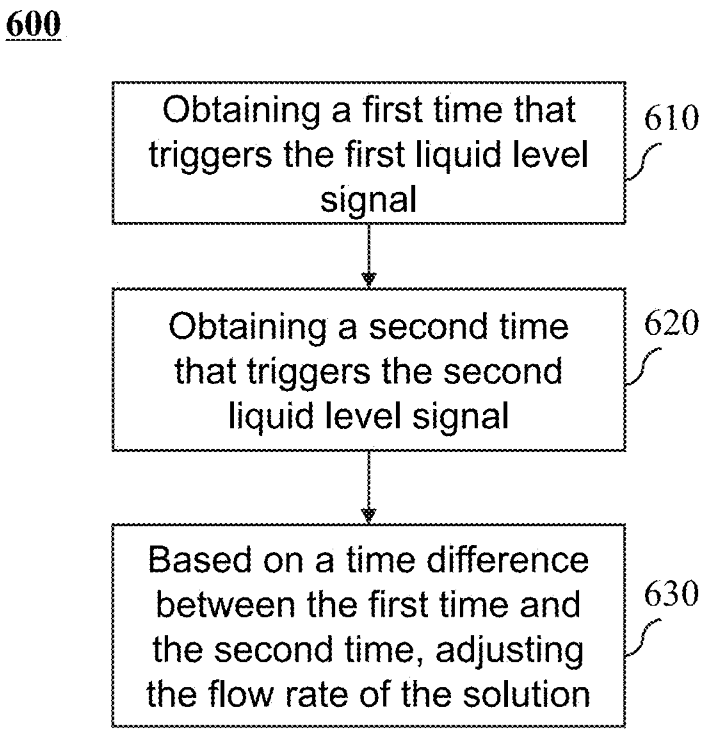
FIG. 6 is a flowchart illustrating a controlling method for an exemplary biological filtration system according to some embodiments of the present disclosure.

FIG. 6 is a flowchart illustrating a controlling method for an exemplary biological filtration system according to some embodiments of the present disclosure.

Referring to FIG. 6, in some embodiments, a controlling method for a biological filtration system may include a process 600. In some embodiments, the process 600 may be performed by the processor and includes the following steps:

Step 610, obtaining a first time that triggers the first liquid level signal.

In some embodiments, when the first sensor 111 or the fourth sensor 204 obtains the first liquid level signal, the processor records the first time that triggers the first liquid level signal simultaneously.

Step 620, obtaining a second time that triggers the second liquid level signal.

In some embodiments, when the second sensor 112 or the third sensor 203 obtains the second liquid level signal, the processor records the second time that triggers the second liquid level signal simultaneously.

Step 630, based on a time difference between the first time and the second time, adjusting the flow rate of the solution.

In some embodiments, the processor may pre-store parameters such as the preset time difference, the volume of the chamber, the cross-sectional area of the chamber, and the preset flow rate. In some embodiments, the processor adjusts the flow rate of the solution based on the relationship between the time difference between the first time and the second time and the preset time difference. For more description of the preset time difference, refer to the process 700. In some embodiments, the processor may calculate the flow rate of the solution in the liquid chamber 102 based on the time difference between the first time and the second time, combined with parameter information such as the volume of the chamber and the cross-sectional area of the chamber, and adjust the flow rate of the solution in the liquid chamber 102 to meet the preset flow rate, so that the flow rate of the solution in the liquid chamber 102 is optimized for efficiency and filtration effect.

Figure 7:
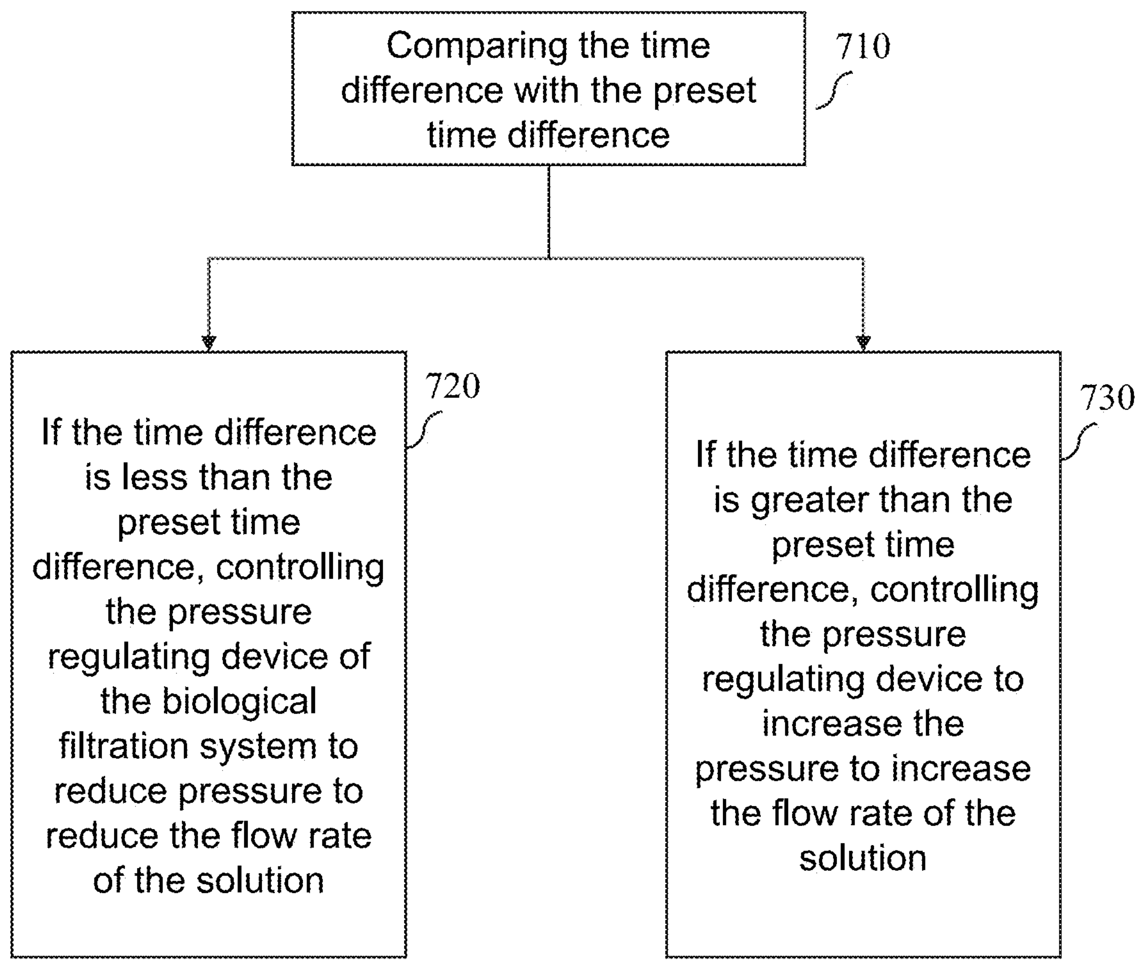
FIG. 7 is a flowchart illustrating a controlling method for an exemplary biological filtration system according to some embodiments of the present disclosure.

FIG. 7 is a flowchart illustrating a controlling method for an exemplary biological filtration system according to some embodiments of the present disclosure.

Referring to FIG. 7, step 630 may include a process 700. In some embodiments, the process 700 may be performed by the processor and includes the following steps:

Step 710, comparing the time difference with the preset time difference.

In some embodiments, the processor may retrieve a pre-stored preset time difference from the storage medium, and the preset time difference may be the one-way time required for the liquid level of the solution to move between the high liquid level line and the low liquid level line under the premise of satisfying the optimization of efficiency and filtration effect. In some embodiments, the preset time difference may be a time value. In some embodiments, the preset time difference may be a time range.

In some embodiments, the processor calculates the time difference between the first time and the second time, and compares the time difference between the first time and the second time with the preset time difference, and adjusts the flow rate of the solution through the first pressure regulating device 118 and/or the second pressure regulating device 119 according to the comparison result. For more descriptions of the first pressure regulating device 118 and the second pressure regulating device 119, referring to FIGS. 1A to 4B and their related descriptions.

Step 720, if the time difference is less than the preset time difference, controlling the pressure regulating device of the biological filtration system to reduce pressure to reduce the flow rate of the solution. Reducing pressure may be reducing the positive pressure pumped by the positive pressure pump 103 and/or reducing the negative pressure pumped by the negative pressure pump 104.

In some embodiments, if the time difference between the first time and the second time is less than the preset time difference, it means that the flow rate of the solution is too fast, and the positive and/or negative pressure within the liquid chamber 102 may be reduced by the first pressure regulating device 118 and/or the second pressure regulating device 119.

Step 730, if the time difference is greater than the preset time difference, controlling the pressure regulating device to increase the pressure to increase the flow rate of the solution.

In some embodiments, if the time difference between the first time and the second time is greater than the preset time difference, it means that the flow rate of the solution is too slow, and the positive and/or negative pressure within the liquid chamber 102 may be increased by the first pressure regulating device 118 and/or the second pressure regulating device 119.

In some embodiments, if the time difference between the first time and the second time is equal to the preset time difference or within the range of the preset time difference, it means that the flow rate of the solution satisfies the optimization of efficiency and filtration effect, and there is no need to adjust the flow rate of the solution.

In some embodiments, the processor may continuously adjust the first pressure regulating device and the second pressure regulating device based on a Proportion Integration Differentiation (PID) control algorithm, until the time difference between the first time and the second time is equal to the preset time difference or within the range of the preset time difference.

Figure 8:
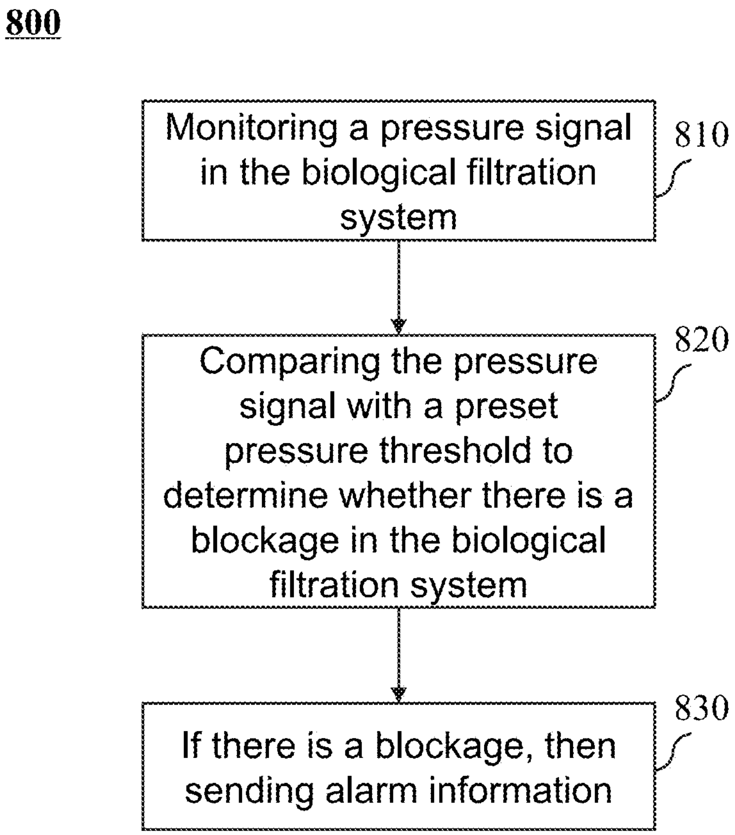
FIG. 8 is a flowchart illustrating a controlling method for an exemplary biological filtration system according to some embodiments of the present disclosure.

FIG. 8 is a flowchart illustrating a controlling method for an exemplary biological filtration system according to some embodiments of the present disclosure.

Referring to FIG. 8, in some embodiments, a controlling method for a biological filtration system may include a process 800. In some embodiments, the process 800 may be performed by the processor and includes the following steps:

Step 810, monitoring a pressure signal in the biological filtration system.

In some embodiments, the pressure signal may be the pressure value of the solution or the pressure value of the gas in the conduit of the biological filtration system.

In some embodiments, the biological filtration system further includes at least one pressure sensor 124 for detecting the pressure signal of the solution and/or the gas. For more description of the pressure sensor 124, referring to FIGS. 1A to 4B and related descriptions. In some embodiments, the processor may obtain the pressure signal collected by the pressure sensor 124 and process the pressure signal.

Step 820, comparing the pressure signal with a preset pressure threshold to determine whether there is a blockage in the biological filtration system.

In some embodiments, the preset pressure threshold may be a pressure threshold for the solution or the gas when it may not flow or flow very slowly.

In some embodiments, the processor compares the pressure signal collected by the pressure sensor 124 with the value of a preset pressure threshold, and determines whether there is a blockage in the biological filtration system based on the comparison result. In some embodiments, if the pressure signal is less than the preset pressure threshold, it means that there is no blockage in the biological filtration system, and the solution or gas may flow freely. In some embodiments, if the pressure signal is greater than or equal to a preset pressure threshold, it means that there is a blockage in the biological filtration system, and the solution or gas may not flow or flow very slowly.

Step 830, if there is a blockage, then sending alarm information.

In some embodiments, if the processor determines that the pressure signal is greater than or equal to the preset pressure threshold, it means that the biological filtration system is blocked, and the processor may send the alarm information to prompt the relevant personnel, so that the relevant personnel may check and maintain the biological filtration system in time.

Figure 9:
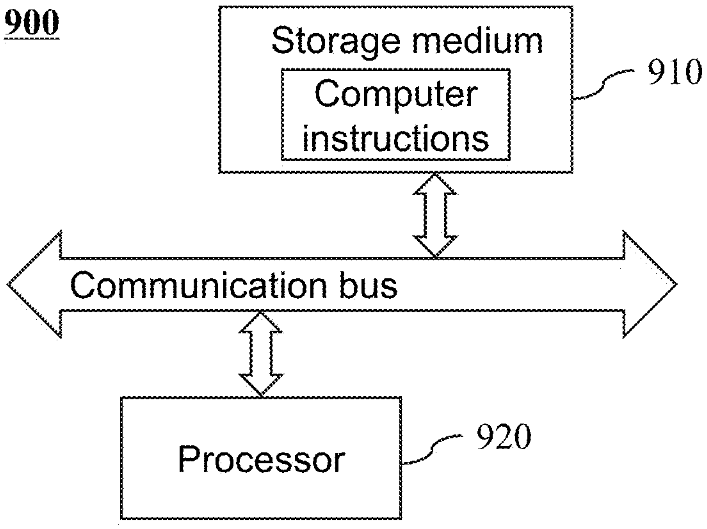
FIG. 9 is a schematic diagram illustrating an exemplary structure of a processing device of a biological filtration system according to some embodiments of the present disclosure.

FIG. 9 is a schematic diagram illustrating an exemplary structure of a processing device of a biological filtration system according to some embodiments of the present disclosure.

As shown in FIG. 9, the biological filtration system in embodiment 1 to embodiment 4 may further include a processing device 900. In some embodiments, the processing device 900 includes a storage medium 910, a processor 920, and a communication bus. The storage medium 910 and the processor 920 may implement a communication process through the communication bus. The processor 920 may be configured to execute the controlling method for the biological filtration system provided by any of the above embodiments of the present disclosure.

In some embodiments, the processor 920 may be implemented by a central processing unit, a server, a terminal device, or any other possible processing device. In some embodiments, the above-mentioned central processing unit, server, terminal device or other processing device may be implemented on a cloud platform. In some embodiments, the above-mentioned central processing unit, server or other processing device may be interconnected with various terminal devices, and the terminal device may complete information processing work or part of the information processing work.

In some embodiments, the storage medium 910 (or a computer-readable storage medium) may store data and/or instructions. In some embodiments, the storage medium 910 may store computer instructions, and the processor 920 (or a computer) may read the computer instructions to execute the controlling method for the biological filtration system provided in any embodiment of the present disclosure. In some embodiments, the storage device may include mass memory, removable memory, volatile read-write memory, read-only memory (ROM), the like, or any combination thereof. In some embodiments, the storage device may be implemented on a cloud platform.

The possible beneficial effects of the embodiments of the present disclosure include but are not limited to: (1) in some embodiments, the filter device and the liquid chamber are integrally formed, the filter device includes a filter portion and a storage portion, the liquid chamber is integrated in the storage portion and directly connected to the filter portion, so that the integrated design of the liquid chamber inside the filter device makes the design more compact, which not only simplifies the structure of the biological filtration system, but also reduces the volume of space occupied by the filter device and the liquid chamber; (2) in some embodiments, the liquid chamber includes a single chamber that is directly connected to the top end of the filter device, which can reduce the amount of solution circulating outside the bioreactor and filter device; (3) in some embodiments, the liquid chamber includes a single chamber, and the chamber is connected to the top end or bottom end of the filter device through a conduit, which can increase the flexibility of the arrangement position of the liquid chamber; (4) in some embodiments, the liquid chamber and the filter device are arranged separately and includes a plurality of chambers, each chamber is in fluid communication with the positive pressure pump and the negative pressure pump, and each chamber is in communication with the filter device, so that the positive pressure pump delivers positive pressure to part of the chambers, while the negative pressure pump delivers negative pressure to another part of the chambers to improve the filtration efficiency of the solution between the filter device and the bioreactor; (5) by setting the volume and/or the negative pressure value of the negative pressure buffer chamber, the height of the solution rising in the liquid chamber may be controlled, so as to prevent the solution from rising too high and overflowing from the top end of the liquid chamber. In addition, the negative pressure buffer chamber may balance the positive pressure in the circulation loop of the biological filtration system, reduce the pressure disturbance in the circulation loop, and improve the safety and controllability of the biological filtration system. It should be noted that different embodiments may have different beneficial effects, and in different embodiments, the possible beneficial effects may be any one or a combination thereof, or any other possible beneficial effects.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure, or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures, or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or collocation of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer-readable program code embodied thereon.

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software-only solution—e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claimed subject matter may lie in less than all features of a single foregoing disclosed embodiment.

Finally, it should be understood that the embodiments described in the present disclosure are only used to illustrate the principles of the embodiments of the present disclosure. Other variations may also fall within the scope of the present disclosure. Therefore, as an example and not a limitation, alternative configurations of the embodiments of the present disclosure may be regarded as consistent with the teaching of the present disclosure. Accordingly, the embodiments of the present disclosure are not limited to the embodiments introduced and described in the present disclosure explicitly.

What is claimed is:

1. A biological filtration system for filtering a solution in a bioreactor, comprising:

a filter device having a top end and a bottom end, one of the top end and the bottom end being in fluid communication with the bioreactor for filtering the solution in the bioreactor;

a liquid chamber in fluid communication with the other one of the top end and the bottom end for storing a solution in the filter device;

a positive pressure pump, in fluid communication with the liquid chamber, for driving the solution to flow from the liquid chamber to the bioreactor; and a negative pressure pump, in fluid communication with the liquid chamber, for driving the solution to flow from the bioreactor to the liquid chamber;

a negative pressure buffer chamber, wherein the negative pressure buffer chamber is disposed on a flow path between the negative pressure pump and the liquid chamber; the negative pressure buffer chamber is configured to control a rising height of the solution in the liquid chamber, and wherein when the flow path between the negative pressure buffer chamber and the liquid chamber is in the non-conductive state, a flow path between the negative pressure buffer chamber and the negative pressure pump is in a conductive state, the negative pressure pump provides a negative pressure to the negative pressure buffer chamber; after the negative pressure in the negative pressure buffer chamber reaches a preset pressure value, the negative pressure buffer chamber is working, the flow path between the negative pressure buffer chamber and the negative pressure pump is in the non-conductive state;

wherein a solenoid valve is installed between the negative pressure buffer chamber and the liquid chamber, the solenoid valve is used to control opening and closing of a connection between the negative pressure buffer chamber and the liquid chamber; the system further comprising a processor configured to:

determine a maximum height that the liquid chamber allows the solution to rise, and calculate a first negative pressure value that the negative pressure buffer chamber needs to provide to the liquid chamber to reach the maximum height;

the negative pressure pump provides a second negative pressure of the first negative pressure value into the negative pressure buffer chamber, and the processor controls a second pressure regulating device between the negative pressure buffer chamber and the negative pressure pump to close;

when a load cell detects that the second negative pressure in the negative pressure buffer chamber drops to a set value, the processor controls the solenoid valve to close.

2. The biological filtration system of claim 1, wherein the filter device comprises a filter portion and a storage portion, wherein the filter portion is disposed close to the bottom end of the filter device, the storage portion is disposed close to the top end of the filter device, the storage portion is configured as a hollow chamber to form the liquid chamber, and the storage portion is in direct communication with the filter portion.

3. The biological filtration system of claim 1, wherein the liquid chamber comprises a single chamber that directly interfaces with the top end of the filter device or is connected to the top end or the bottom end of the filter device by a conduit; or wherein the liquid chamber comprises a plurality of chambers, each of the plurality of chambers being connected to the top end or the bottom end of the filter device through a conduit.

4. The biological filtration system of claim 2, wherein the biological filtration system comprises a first conduit, wherein the bottom end of the filter device is connected to the bioreactor through the first conduit, the positive pressure pump is used to drive the solution in the filter device to flow to the bioreactor along the first conduit, and the negative pressure pump is used to drive the solution in the bioreactor to flow to the filter device along the first conduit.

5. The biological filtration system of claim 2, wherein the biological filtration system comprises a second conduit and a third conduit, wherein the bottom end of the filter device is connected to the bioreactor through the second conduit and the third conduit, the second conduit is disposed with a first one-way valve, so that the solution in the filter device flows to the bioreactor in one direction, and the third conduit is disposed with a second one-way valve, so that the solution in the bioreactor flows to the filter device in one direction.

6. The biological filtration system of claim 2, wherein the biological filtration system comprises a fourth conduit, a fifth conduit and a sixth conduit, wherein one of the top end and the bottom end of the filter device is connected to the liquid chamber through the fourth conduit, the other one of the top end and the bottom end of the filter device is connected to the bioreactor through the fifth conduit, the liquid chamber is connected to the bioreactor through the sixth conduit, the positive pressure pump is used to drive the solution in the liquid chamber to flow to the bioreactor through the filter device, and the negative pressure pump is used to drive the solution in the bioreactor to flow to the liquid chamber; or the positive pressure pump is used to drive the solution in the liquid chamber to flow to the bioreactor, and the negative pressure pump is used to drive the solution in the bioreactor to flow to the liquid chamber through the filter device.

7. The biological filtration system of claim 1, wherein the biological filtration system further comprises a first sensor, wherein the first sensor is configured to detect liquid level information in the liquid chamber and is disposed on a top portion of the liquid chamber at a preset interval; and a second sensor, configured to detect the liquid level information in the liquid chamber and disposed on a bottom portion of the liquid chamber.

8. The biological filtration system of claim 1, wherein the biological filtration system further comprises a third sensor and a fourth sensor for detecting liquid level information in the filter device, and the filter device includes a reaction liquid port and a retentate liquid port, wherein the third sensor is disposed at the reaction liquid port, and the fourth sensor is disposed at the retentate liquid port.

9. The biological filtration system of claim 1, the biological filtration system further comprises one or more of a gas purifier, a cooling device, a liquid storage box, a check valve, and/or a heating device; wherein the gas purifier disposed on a flow path connecting the positive pressure pump and the negative pressure pump in the liquid chamber;

the cooling device is provided within the liquid chamber for cooling air entering the gas purifier;

the liquid storage box is disposed on a flow path between the gas purifier and the negative pressure pump, and the liquid storage box is used to collect a condensed water;

the check valve is disposed on a flow path between the gas purifier and the negative pressure pump, and is used to prevent the condensed water from flowing back into the gas purifier;

the heating device is disposed for the gas purifier and/or the liquid chamber.

10. The biological filtration system of claim 1, wherein the biological filtration system further comprises a first pressure regulating device and the second pressure regulating device, wherein the first pressure regulating device is disposed at an outlet of the positive pressure pump and is used to adjust a pumping gas pressure of the positive pressure pump, and the second pressure regulating device is disposed at an outlet of the negative pressure pump and is used to adjust a suction gas pressure of the negative pressure pump.

11. The biological filtration system of claim 1, wherein the biological filtration system further comprises a pressure relief bypass, wherein the pressure relief bypass is disposed on a flow path between the liquid chamber and the positive pressure pump and/or the negative pressure pump for releasing gas pressure in the biological filtration system.

12. The biological filtration system of claim 1, wherein the filter device is disposed with a penetrating liquid port, and the biological filtration system further comprises a collection container and a flow controlling device, wherein the penetrating liquid port is connected to the collection container, the flow controlling device is disposed between the collection container and the filter device, and is used to control a flow rate of the solution in the filter device to the collection container.

13. The biological filtration system of claim 1, further comprising the processor configured to:

obtain a first liquid level signal in the filter device or the liquid chamber;

control the positive pressure pump to drive the solution in the filter device to flow to the bioreactor based on the first liquid level signal;

obtain a second liquid level signal in the filter device or the liquid chamber; and control the negative pressure pump to drive the solution in the bioreactor to flow to the filter device based on the second liquid level signal;

obtain a first time of triggering the first liquid level signal;

obtain a second time of triggering the second liquid level signal; and adjust, based on a time difference between the first time and the second time, a flow rate of the solution.

14. A controlling method for a biological filtration system, wherein the biological filtration system comprises a filter device having a top end and a bottom end, one of the top end and the bottom end being in fluid communication with the bioreactor for filtering the solution in the bioreactor;

a liquid chamber in fluid communication with the other one of the top end and the bottom end for storing a solution in the filter device;

a positive pressure pump, in fluid communication with the liquid chamber, for driving the solution to flow from the liquid chamber to the bioreactor; and a negative pressure pump, in fluid communication with the liquid chamber, for driving the solution to flow from the bioreactor to the liquid chamber;

a negative pressure buffer chamber, wherein the negative pressure buffer chamber is disposed on a flow path between the negative pressure pump and the liquid chamber; the negative pressure buffer chamber is configured to control a rising height of the solution in the liquid chamber, and wherein when the flow path between the negative pressure buffer chamber and the liquid chamber is in a non-conductive state, and a flow path between the negative pressure buffer chamber and the negative pressure pump is in a conductive state, the negative pressure pump provides a negative pressure to the negative pressure buffer chamber; after the negative pressure in the negative pressure buffer chamber reaches a preset pressure value, the negative pressure buffer chamber is working, the flow path between the negative pressure buffer chamber and the negative pressure pump is in the non-conductive state, wherein a solenoid valve is installed between the negative pressure buffer chamber and the liquid chamber, the solenoid valve is used to control opening and closing of a connection between the negative pressure buffer chamber and the liquid chamber; the system further comprising a processor configured to:

determine a maximum height that the liquid chamber allows the solution to rise, and calculate a first negative pressure value that the negative pressure buffer chamber needs to provide to the liquid chamber to reach the maximum height;

the negative pressure pump provides a second negative pressure of the first negative pressure value into the negative pressure buffer chamber, and the processor controls a second pressure regulating device between the negative pressure buffer chamber and the negative pressure pump to close;

when a load cell detects that the second negative pressure in the negative pressure buffer chamber drops to a set value, the processor controls the solenoid valve to close; and the controlling method comprises:

obtaining a first liquid level signal in the filter device or the liquid chamber;

controlling the positive pressure pump to drive the solution in the filter device to flow to the bioreactor based on the first liquid level signal;

obtaining a second liquid level signal in the filter device or the liquid chamber; and controlling the negative pressure pump to drive the solution in the bioreactor to flow to the filter device based on the second liquid level signal.

15. The biological filtration system of claim 3, wherein the negative pressure pump is in fluid communication with the plurality of chambers through a second multiway conduit; the second multiway conduit includes a second main circuit and a plurality of second branches, one end of the second main circuit is connected to the positive pressure pump, and the plurality of second branches are respectively connected to the plurality of chambers one by one;

the negative pressure buffer chamber is disposed on the second main circuit of the second multiway conduit, and the negative pressure buffer chamber is configured as a hollow chamber.

16. The biological filtration system of claim 1, wherein the second pressure regulating device is disposed between the negative pressure pump and the negative pressure buffer chamber, and the second pressure regulating device is used to control a suction gas pressure of the negative pressure pump to the negative pressure buffer chamber; when a pressure in the negative pressure buffer chamber reaches the preset pressure value, the second pressure regulating device is switched to a closed state, so that the flow path between the negative pressure pump and the negative pressure buffer chamber is in the non-conductive state, and the negative pressure pump stops working, and the negative pressure buffer chamber forms a third negative pressure corresponding to the preset pressure value.

17. The biological filtration system of claim 13, wherein to adjust, based on the time difference between the first time and the second time, the flow rate of the solution, the processor is configured to compare the time difference with a preset time difference;

if the time difference is less than the preset time difference, control a pressure regulating device of the biological filtration system to reduce pressure to reduce the flow rate of the solution; and if the time difference is greater than the preset time difference, control the pressure regulating device to increase the pressure to increase the flow rate of the solution.

18. The biological filtration system of claim 13, wherein the processor is further configured to:

monitor a pressure signal in the biological filtration system;

compare the pressure signal with a preset pressure threshold to determine whether there is a blockage in the biological filtration system; and if there is a blockage, send an alarm message.

* * * * *